United States Patent
Endo et al.

(10) Patent No.: US 10,564,795 B2
(45) Date of Patent: Feb. 18, 2020

(54) CONTROL METHOD, PROCESSING APPARATUS, AND NON-TRANSITORY COMPUTER-READABLE RECORDING MEDIUM

(71) Applicant: Panasonic Intellectual Property Management Co., Ltd., Osaka (JP)

(72) Inventors: Mitsuru Endo, Osaka (JP); Noriaki Horii, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 384 days.

(21) Appl. No.: 15/360,340

(22) Filed: Nov. 23, 2016

(65) Prior Publication Data

US 2017/0160878 A1 Jun. 8, 2017

(30) Foreign Application Priority Data

Dec. 2, 2015 (JP) ................................. 2015-235918

(51) Int. Cl.
*G06Q 50/16* (2012.01)
*A61B 5/00* (2006.01)
(Continued)

(52) U.S. Cl.
CPC .......... *G06F 3/0481* (2013.01); *A61B 5/4803* (2013.01); *A61B 5/7264* (2013.01);
(Continued)

(58) Field of Classification Search
CPC ........ G06F 3/0481; G06F 3/1454; G06F 3/16; G06F 19/363; G06Q 50/16; A61B 5/4803; A61B 5/741; A61B 5/7435; A61B 5/7264
See application file for complete search history.

(56) References Cited

U.S. PATENT DOCUMENTS 6,763,342 B1 * 7/2004 Mattern ................. G06N 5/043
706/46
7,337,158 B2 * 2/2008 Fratkina ................. G06N 5/042
706/45

(Continued)

FOREIGN PATENT DOCUMENTS

JP 2001-325104 11/2001
WO 2002/009004 A1 1/2002

OTHER PUBLICATIONS

The Extended European Search Report from the European Patent Office (EPO) dated Sep. 29, 2017 for the related European Patent Application No. 16200966.6.

(Continued)

*Primary Examiner* — Shourjo Dasgupta
(74) *Attorney, Agent, or Firm* — Greenblum & Bernstein, P.L.C.

(57) ABSTRACT

A control method includes displaying a network diagram including nodes of first and second types corresponding to symptoms and illnesses, respectively, the nodes of the second type each being linked to one or more related nodes of the first type via a connection line, emphasizing display of a first node of the first type corresponding to a symptom, the first node corresponding to a question asking about presence or absence of the symptom, acquiring an inputted answer to the question by a user, determining the user's answer to the question, and if the symptom is determined to be present, deleting all nodes from the network diagram except for the first node, one or more second nodes of the second type directly linked to the first node, and one or more third nodes of the first type directly linked to the one or more second nodes.

11 Claims, 18 Drawing Sheets

D1

|  | ILLNESS 1 | ILLNESS 2 | ILLNESS 3 | ILLNESS 4 |
|---|---|---|---|---|
| SYMPTOM A | ○ | ○ |  |  |
| SYMPTOM B | ○ |  | ○ |  |
| SYMPTOM C | ○ |  |  |  |
| SYMPTOM D |  | ○ |  |  |
| SYMPTOM E |  |  | ○ |  |
| SYMPTOM F |  |  |  | ○ |

(51) Int. Cl.
    *G06F 3/01*        (2006.01)
    *G06F 3/14*        (2006.01)
    *G06F 3/0481*    (2013.01)
    *G16H 10/20*    (2018.01)
    *G16H 50/20*    (2018.01)
    *G06F 3/16*        (2006.01)
    *G06F 3/0488*    (2013.01)
    *G06F 3/0489*    (2013.01)

(52) U.S. Cl.
    CPC ............ *A61B 5/741* (2013.01); *A61B 5/7435* (2013.01); *G06F 3/1454* (2013.01); *G06Q 50/16* (2013.01); *G16H 10/20* (2018.01); *G16H 50/20* (2018.01); *G06F 3/0488* (2013.01); *G06F 3/0489* (2013.01); *G06F 3/16* (2013.01)

(56) References Cited

U.S. PATENT DOCUMENTS

| | | | |
|---|---|---|---|
| 2003/0140063 A1* | 7/2003 | Pizzorno | G16H 50/20 |
| 2006/0030890 A1 | 2/2006 | Cosentino et al. | |
| 2012/0296980 A1* | 11/2012 | Pace | G06Q 10/10 |
| | | | 709/205 |
| 2015/0278695 A1* | 10/2015 | Shah | G06N 5/00 |
| | | | 706/11 |
| 2016/0117058 A1* | 4/2016 | Maruyama | G06F 16/00 |
| | | | 715/854 |
| 2017/0039577 A1* | 2/2017 | Gauthier | G06F 16/26 |

OTHER PUBLICATIONS

Hui Yang: "User Centered Design of Visual Analytics and its Applications in Healthcare", Dec. 1, 2014 (Dec. 1, 2014), XP055407012, Retrieved from the Internet: URL:https://etda.libraries.psu.edu/files/final_submissions/10293 [retrieved on Sep. 15, 2017].

Zhang Zhiyuan et al: "The Five Ws for Information Visualization with Application to Healthcare Informatics", IEEE Transactions on Visualization and Computer Graphics, IEEE Service Center, Los Alamitos, CA, US, vol. 19, No. 11 , Nov. 1, 2013 (Nov. 1, 2013), pp. 1895-1910, XP011526649.

* cited by examiner

| | ILLNESS 1 | ILLNESS 2 | ILLNESS 3 | ILLNESS 4 |
|---|---|---|---|---|
| SERIOUSNESS | NOT HAVING | HAVING | NOT HAVING | NOT HAVING |
| SYMPTOM A | ○ | ○ | | |
| SYMPTOM B | ○ | | ○ | |
| SYMPTOM C | ○ | | | |
| SYMPTOM D | | ○ | | |
| SYMPTOM E | | | ○ | |
| SYMPTOM F | | | | ○ |

D2

CONTROL METHOD, PROCESSING APPARATUS, AND NON-TRANSITORY COMPUTER-READABLE RECORDING MEDIUM

BACKGROUND

1. Technical Field

The present disclosure relates to a control method, a processing apparatus, and a non-transitory computer-readable recording medium.

2. Description of the Related Art

In the related art, techniques and apparatuses that narrow down information through interactions by using classification trees are disclosed.

However, while answering sequential questions to identify desired information among a plurality of pieces of predetermined information by using a technique and an apparatus of the related art, the respondent may feel anxious or irksome if there are a large number of questions before identification of the desired information.

In addition, if the respondent feels anxious or irksome, the respondent might not be in their regular state of mind, and correct answers might not be acquired. If correct answers are not acquired, it is necessary to search for information again, which increases the processing load and power consumption of the apparatus.

SUMMARY

In one general aspect, the techniques disclosed here feature a control method executed by a processor for controlling a display connected to the processor and a memory, the processor being connected to an input that receives an inputted answer to a presented question, the control method including: causing the display to display a network diagram, the network diagram being stored in the memory and including a plurality of nodes of a first type corresponding to a plurality of symptoms and a plurality of nodes of a second type corresponding to a plurality of illnesses, the plurality of nodes of the second type each being linked to one or more related nodes of the first type among the plurality of nodes of the first type via a connection line; causing the display to emphasize a display of a first node of the first type corresponding to the presented question, the presented question asking about presence or absence of one symptom among the plurality of symptoms, the first node corresponding to the one symptom; acquiring the inputted answer to the presented question from the input, the inputted answer being input to the input by a user; determining an answer to the presented question from the inputted answer; and if it is determined that the user has answered that the one symptom is present, causing the display to delete all nodes from the network diagram except for the first node, one or more second nodes of the second type directly linked to the first node, and one or more third nodes of the first type directly linked to the one or more second nodes of the second type directly linked to the first node.

A control method according to an embodiment of the present disclosure can suppress a respondent's feeling of anxiety or irksomeness at the time of engaging in questions and answers in search of desired information.

It should be noted that general or specific embodiments may be implemented as a system, a method, an integrated circuit, a computer program, a recording medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

Figure 1:
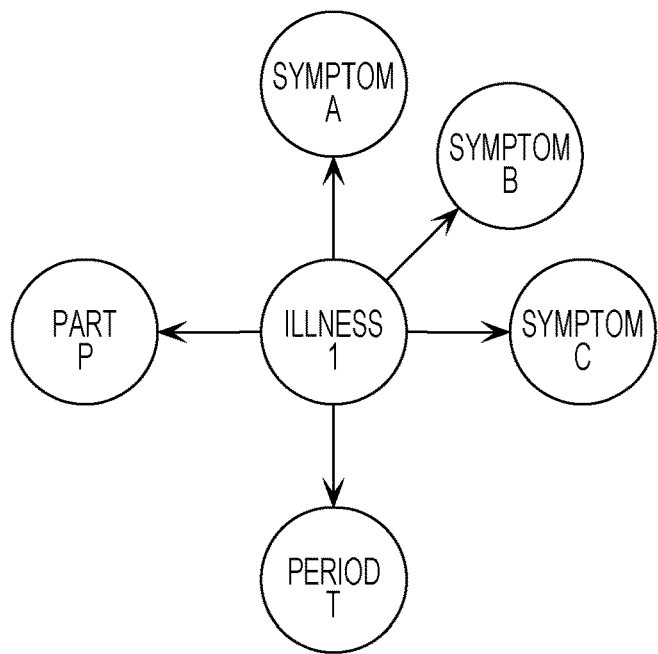
FIG. 1 is a first explanation diagram used to describe a method for identifying an illness on the basis of checking of symptoms.

DETAILED DESCRIPTION (1) A control method according to an aspect of the present disclosure is a control method executed by a processor for controlling a display connected to the processor and a memory, the processor being connected to an input that receives an inputted answer to a presented question, the control method including: causing the display to display a network diagram, the network diagram being stored in the memory and including a plurality of nodes of a first type corresponding to a plurality of symptoms and a plurality of nodes of a second type corresponding to a plurality of illnesses, the plurality of nodes of the second type each being linked to one or more related nodes of the first type among the plurality of nodes of the first type via a connection line; causing the display to emphasize a display of a first node of the first type corresponding to the presented question, the presented question asking about presence or absence of one symptom among the plurality of symptoms, the first node corresponding to the one symptom; acquiring the inputted answer to the presented question from the input, the inputted answer being input to the input by a user; determining an answer to the presented question from the inputted answer; and if it is determined that the user has answered that the one symptom is present, causing the display to delete all nodes from the network diagram except for the first node, one or more second nodes of the second type directly linked to the first node, and one or more third nodes of the first type directly linked to the one or more second nodes of the second type directly linked to the first node.

Accordingly, by seeing a presented network, a user can look through the questions (presence and absence of symptoms) and information (candidate illnesses) to answer the questions displayed in the network. Thus, the user can search for one piece of information by providing affirmative answers to the questions independently of the order of sequential questions that are asked by using a decision tree. In this manner, a search support apparatus can suppress the user's feeling of anxiety or irksomeness at the time of engaging in questions and answers in search of desired information. Unless the user feels anxious or irksome, it is unnecessary to search for information again as a result of the anxiety or irksomeness, thereby avoiding an increase in the processing load and power consumption of the apparatus.

(2) In the above aspect, it may be determined whether or not a number of the one or more second nodes of the second type directly linked to the first node is less than or equal to a predetermined number. If it is determined that the number of the one or more second nodes of the second type directly linked to the first node is greater than the predetermined number, a process may be repeated until the number of the one or more second nodes of the second type directly linked to the first node becomes less than or equal to the predetermined number, the process including causing the display to emphasize display, acquiring the inputted answer, determining the answer, causing the display to perform deletion, and determining whether or not the number of the one or more second nodes of the second type directly linked to the first node is less than or equal to the predetermined number.

(3) In the above aspect, the predetermined number may be one.

(4) In the above aspect, the memory may further store first information and second information, the first information indicating each of the plurality of illnesses and a degree of seriousness of a corresponding illness, the second information indicating a question to be presented to the user. If it is determined that the one or more second nodes of the second type directly linked to the first node include a single second node, it may be determined whether or not a degree of seriousness of an illness corresponding the single second node is greater than or equal to a threshold based on the first information. If it is determined that the degree of seriousness of the illness corresponding to the single second node is greater than or equal to the threshold, the display may be caused to display at least a first node that does not correspond to the presented question based on the second information.

(5) In the above aspect, it may be determined whether or not a number of the one or more second nodes of the second type directly linked to the first node is less than or equal to a predetermined number. If it is determined that the number of the one or more second nodes of the second type directly linked to the first node is greater than the predetermined number, the display may be prohibited from displaying the network diagram.

(6) In the above aspect, the display may be a first display device for a doctor who is in charge of a diagnosis of an illness of the user, the processor may be connected to a second display device for the user, the second display device being different from the first display device, and the second display device may be caused to perform a same display as the first display device.

(7) In the above aspect, the display may be a first display device for a doctor who is in charge of a diagnosis of an illness of the user, the processor may be connected to a second display device for the user, the second display device being different from the first display device, and the second display device may be prevented from performing a same display as the first display device.

(8) In the above aspect, the input may include at least one of a microphone, a keyboard, and a touch panel.

(9) A control method according to another aspect of the present disclosure is a control method for controlling a display connected to a processor and a memory, the processor being connected to an input that receives an inputted answer to a presented question, the control method including: causing the display to display a network diagram, the network diagram being stored in a memory and including a plurality of nodes of a first type corresponding to a plurality of real estate property conditions and a plurality of nodes of a second type corresponding to a plurality of real estate properties, the plurality of nodes of the second type each being linked to one or more related nodes of the first type among the plurality of nodes of the first type via a connection line; causing the display to emphasize a display of a first node of the first type corresponding to the presented question, the presented question asking about necessity for one condition among the plurality of real estate property conditions, the first node corresponding to the one condition; acquiring the inputted answer to the presented question from the input, the inputted answer being input to the input by a user; determining an answer to the presented question from the inputted answer; and if it is determined that the user has answered that the one condition among the plurality of real estate property conditions is necessary, causing the display to delete all nodes from the network diagram except for the first node, one or more second nodes of the second type directly linked to the first node, and one or more third nodes of the first type directly linked to the one or more second nodes of the second type directly linked to the first node.

(10) A control method according to another aspect of the present disclosure is a control method for controlling a display connected to a processor and a memory, the processor being connected to an input that receives an inputted answer to a presented question, the control method including: causing the display to display a network diagram, the network diagram being stored in a memory and including a plurality of nodes of a first type corresponding to a plurality of itinerary conditions and a plurality of nodes of a second type corresponding to a plurality of itineraries, the plurality of nodes of the second type each being linked to one or more related nodes of the first type among the plurality of nodes of the first type via a connection line; causing the display to emphasize a display of a first node of the first type corresponding to the presented question, the presented question asking about necessity for one condition among the plurality of itinerary conditions, the first node corresponding to the one condition; acquiring the inputted answer to the presented question from the input, the inputted answer being input to the input by a user; determining an answer to the presented question from the inputted answer; and if it is determined that the user has answered that the one condition among the plurality of itinerary conditions is necessary, causing the display to delete all nodes from the network diagram except for the first node, one or more second nodes of the second type directly linked to the first node, and one or more third nodes of the first type directly linked to the one or more second nodes of the second type directly linked to the first node.

(11) A control method according to another aspect of the present disclosure is a control method for controlling a display connected to a processor and a memory, the processor being connected to an input that receives an inputted answer to a presented question, the control method including: causing the display to display a network diagram, the network diagram being stored in a memory and including a plurality of nodes of a first type corresponding to a plurality of fault conditions of a predetermined apparatus and a plurality of nodes of a second type corresponding to a plurality of remedial measures for the fault conditions of the predetermined apparatus, the plurality of nodes of the second type each being linked to one or more related nodes of the first type among the plurality of nodes of the first type via a connection line; causing the display to emphasize a display of a first node of the first type corresponding to the presented question, the presented question asking about presence or absence of one fault condition among the plurality of fault conditions, the first node corresponding to the one fault condition; acquiring the inputted answer to the presented question from the input, the inputted answer being input to the input by a user; determining an answer to the presented question from the inputted answer; and if it is determined that the user has answered that the one fault condition is present, causing the display to delete all nodes from the network diagram except for the first node, one or more second nodes of the second type directly linked to the first node, and one or more third nodes of the first type directly linked to the one or more second nodes of the second type directly linked to the first node.

It should be noted that general or specific aspects may be implemented as a system, a method, an integrated circuit, a computer program, a computer-readable recording medium such as a compact disk read only memory (CD-ROM), or any selective combination of a system, a method, an integrated circuit, a computer program, and a recording medium.

Embodiments will be specifically described below with reference to the drawings.

It should be noted that any of the following embodiments illustrates a general or specific example. The numerals, shapes, materials, components, the arrangement and connection of components, steps, the order of steps, and the like described in the following embodiments are exemplary and should not limit the present disclosure. In addition, among the components described in the following embodiments, components that are not included in the independent claim indicating the most generic concept are described as optional components.

First Embodiment

This embodiment describes a search support apparatus, a search support method, and the like that can suppress a respondent's (user's) feeling of anxiety or irksomeness at the time of engaging in questions and answers in search of desired information. It should be noted that this embodiment describes, as an example, a method for supporting the identification of an illness of a user who is exhibiting symptoms that are considered to be obvious symptoms (hereinafter also referred to simply as symptoms) of an illness by searching for the illness on the basis of the symptoms by using a search support apparatus or the like. However, the usage of the search support apparatus according to this embodiment is not limited to this example.

FIG. 1 is a first explanation diagram used to describe a method for identifying an illness on the basis of checking of symptoms. As illustrated in FIG. 1, an illness 1 is associated with symptoms A, B, and C of the illness 1, a part P at which the illness 1 occurs, and a period T (e.g., three days or a month) over which a person has the illness 1.

The related art (e.g., Japanese Unexamined Patent Application Publication No. 2001-325104) discloses a technique and an apparatus for identifying the illness 1 of a user through predetermined information processing on the basis of the fact that the user is exhibiting the symptoms A, B, and C. According to this technique, the user is asked sequential questions as to whether or not the user is exhibiting a plurality of symptoms including the symptoms A, B, and C, and on the basis of answers to these questions, an illness (illness 1) of the user is searched and identified from among a plurality of predetermined illnesses. However, if the number of the plurality of predetermined illnesses is large, a large number of questions are necessary. Specifically, in the case of about a thousand illnesses, if a search is performed by using a binary tree, the number of questions in the longest path of the tree is estimated to be ten or more.

If a large number of sequential questions are presented to the user, the user may feel anxious or irksome during answering the questions. If the user feels anxious or irksome, the user might not be in their regular state of mind, and correct answers might not be acquired. If correct answers are not acquired, it is necessary to search for information again, and the processing load and power consumption of the apparatus increase.

The search support apparatus and the search support method according to this embodiment can suppress the user's feeling of anxiety or irksomeness at the time of engaging in questions and answers in search of desired information.

Figure 2:
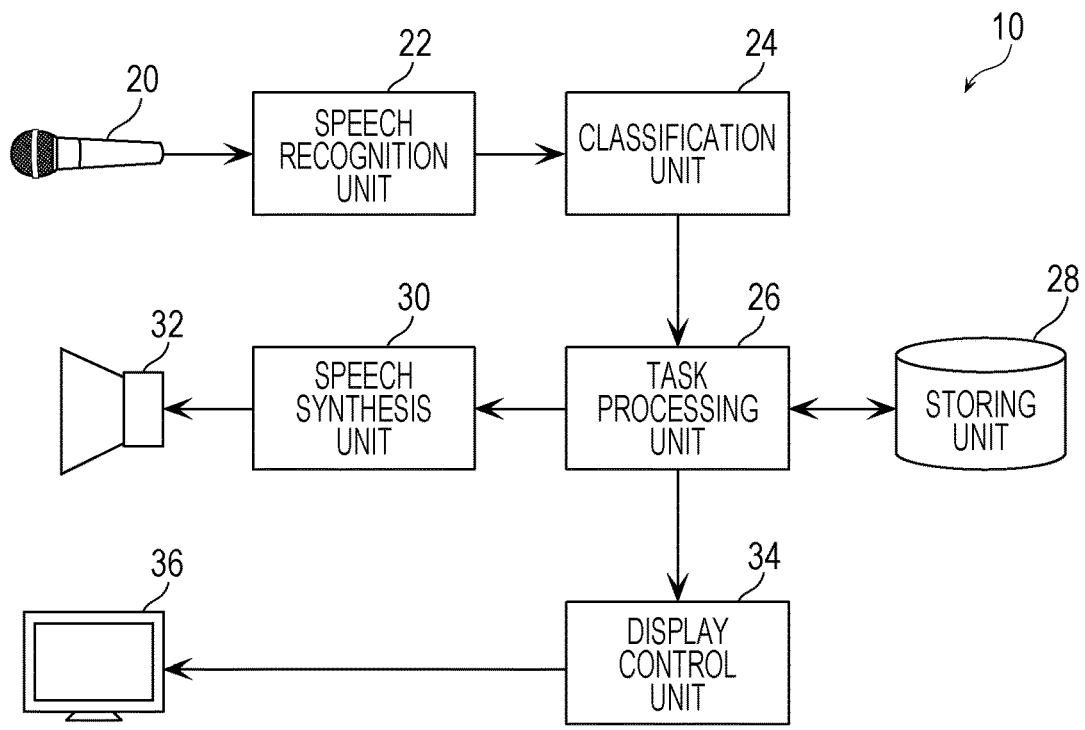
FIG. 2 is a block diagram illustrating a configuration of a search support apparatus according to a first embodiment.

FIG. 2 is a block diagram illustrating a configuration of a search support apparatus 10 according to this embodiment. The search support apparatus 10 is a search support apparatus that supports a search for one piece of information among a plurality of pieces of predetermined information. In the following description, the set of a question presented by the search support apparatus 10 to a user and a user's answer to the question is also referred to as an interaction.

As illustrated in FIG. 2, the search support apparatus 10 includes a microphone 20, a speech recognition unit 22, a classification unit 24, a task processing unit 26, a storage unit 28, a speech synthesis unit 30, a speaker 32, a display control unit 34, and a display device 36. It should be noted that the search support apparatus 10 may be configured in such a manner that the above components are contained in a single housing or that the above components are arranged to be dispersed and connected to each other via a network or the like so that communication can be performed.

The microphone 20 is a sound pickup device that picks up peripheral sounds to generate electric signals corresponding to the picked up sounds.

The speech recognition unit 22 is a processing unit that acquires the electric signals generated by the microphone 20 and that recognizes speech contained in the sounds picked up by the microphone 20 to generate text data. An example of the text data generated by the speech recognition unit 22 is data that can be represented by a character string, such as "I HAVE A FEVER" or "YES". It should be noted that the text data does not have a meaning of the character string. That is, "FEVER" contained in the text data is not associated with "fever" that means a high temperature or with a word having another meaning.

The classification unit 24 is a processing unit that acquires the text data generated by the speech recognition unit 22 to assign a meaning and classify the meaning. The classification unit 24 acquires, for example, "I HAVE A FEVER" as text data from the speech recognition unit 22, and by referring to predetermined interaction data, identifies this text data as an expression "I have a fever" meaning that the person has a high temperature (i.e., meaning is assigned). That is, at this time, a meaning of "fever" meaning a high temperature is assigned to "FEVER" contained in the text data, and "FEVER" is distinguished from a word having another meaning.

In addition, the classification unit 24 classifies text data in accordance with the meaning. Specifically, as the speech indicating that a person has a fever, in addition to the above expression "I have a fever", expressions such as "I got a fever" and "I feel hot" may be possible. The classification unit 24 classifies these expressions as a single meaning of having a fever. In the case where the classification unit 24 acquires "I DO" as text data from the speech recognition unit 22, it is difficult to assign a meaning only by using this text data. However, if the question that has been previously presented is known, the classification unit 24 can classify this expression by determining that it has a meaning of affirming the question. For example, in the case where text data "I DO" is acquired, if the question presented prior to acquiring the text data is "Do you have a fever?", the acquired text data "YES" or "I DO" is classified as a single meaning of Yes. In the above manner, the classification unit 24 deals with variations in expressions that may occur in the speech picked up by the microphone 20.

The task processing unit 26 is a processing unit that searches for the above-described one piece of information on the basis of interactions with the user. Specifically, the task processing unit 26 is a processing unit that acquires text data to which a meaning has been assigned and which has been subjected to meaning classification by the classification unit 24 to register the acquired text data in the storage unit 28. The task processing unit 26 manages the question that has been presented to the user or a plurality of questions to be presented to the user in the form of a decision tree. The task processing unit 26 determines whether or not it is possible to end the search for the desired information on the basis of the decision tree and information that has been acquired from the user up to the current time point. If it is determined that it is not possible to end the search for the desired information on the basis of the information that has been acquired up to the current time point, the task processing unit 26 decides the next question to be presented to the user and generates text data of the decided question. In addition, the task processing unit 26 causes the display device 36 to display the decision tree that the task processing unit 26 is managing and also changes the display mode of the decision tree depending on the interaction, i.e., the progress of the search. The structure of the decision tree and the display mode of the decision tree will be described later in detail.

In addition, the task processing unit 26 causes the display device 36 to display a network that includes, as a node, a condition corresponding to the question presented to the user or a question to be presented, and updates the display mode of the displayed network. The structure of the network and the display mode of the network will be described later in detail.

The storage unit 28 is a storing device that stores various types of information. The storage unit 28 stores an illness data table, a keyword list, an exclusion list, and the like. The illness data table is a table indicating a plurality of predetermined illnesses in association with symptoms of the respective plurality of predetermined illnesses. The keyword list is a list indicating items for which the user has answered. The exclusion list is a list of items that are prohibited from being presented to the user among predetermined items. The above-described table and lists will be specifically described later with reference to examples.

The speech synthesis unit 30 is a processing unit that acquires text data of the next question to be presented to the user, the text data having been generated by the task processing unit 26, to generate electric signals of speech corresponding to this text data.

The speaker 32 is a sound output device that outputs a sound on the basis of the electric signals generated by the speech synthesis unit 30.

The display control unit 34 is a processing unit that generates image data of an image to be displayed on the display device 36 to provide the generated image data to the display device 36. The display control unit 34 acquires, from the task processing unit 26, information indicating the decision tree that the task processing unit 26 is managing and information indicating the display mode of the decision tree to generate image data of the decision tree to be displayed on the display device 36. In addition, the display control unit 34 acquires, from the task processing unit 26, information indicating the network that the task processing unit 26 is managing and information indicating the display mode of the network to generate image data of the network to be displayed on the display device 36. Then, the display control unit 34 provides the generated image data to the display device 36.

The display device 36 is a display device that displays an image on the basis of image data provided from the display control unit 34.

It should be noted that each of the speech recognition unit 22, the classification unit 24, the task processing unit 26, the speech synthesis unit 30, and the display control unit 34 may be implemented by a processor executing a program or may be implemented by using a dedicated circuit.

Figure 3:
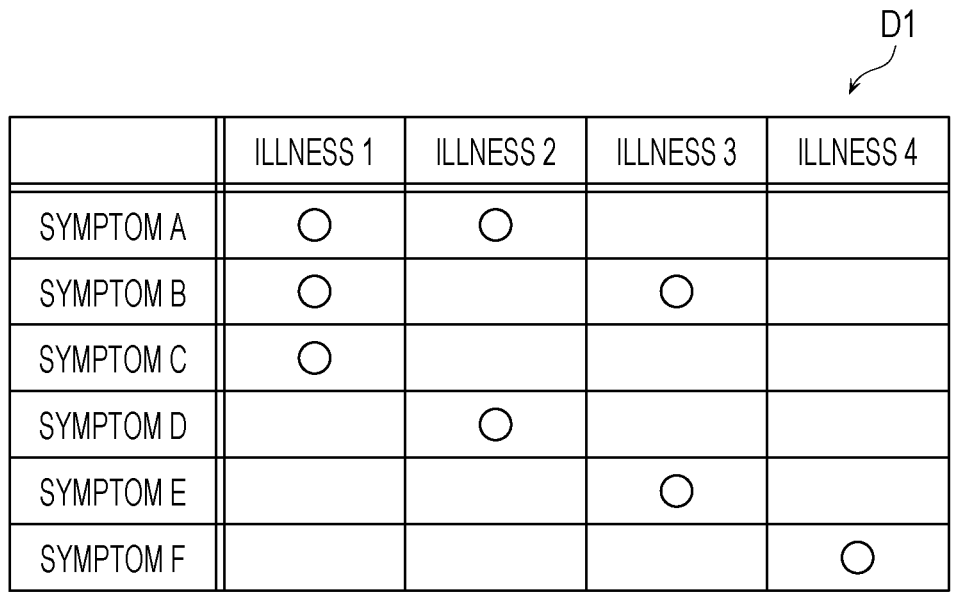
FIG. 3 illustrates data of illnesses in the first embodiment.

FIG. 3 illustrates an illness data table D1 in this embodiment. The illness data table D1 is a table in which a plurality of illnesses and symptoms of the plurality of illnesses are associated with each other.

In the illness data table D1, each column indicates an illness, and circles in each row indicate the symptoms of a corresponding illness. For example, it is indicated that a person having the illness 1 exhibits the symptoms A, B, and C and that a person having an illness 2 exhibits the symptom A and a symptom D.

Figure 4:
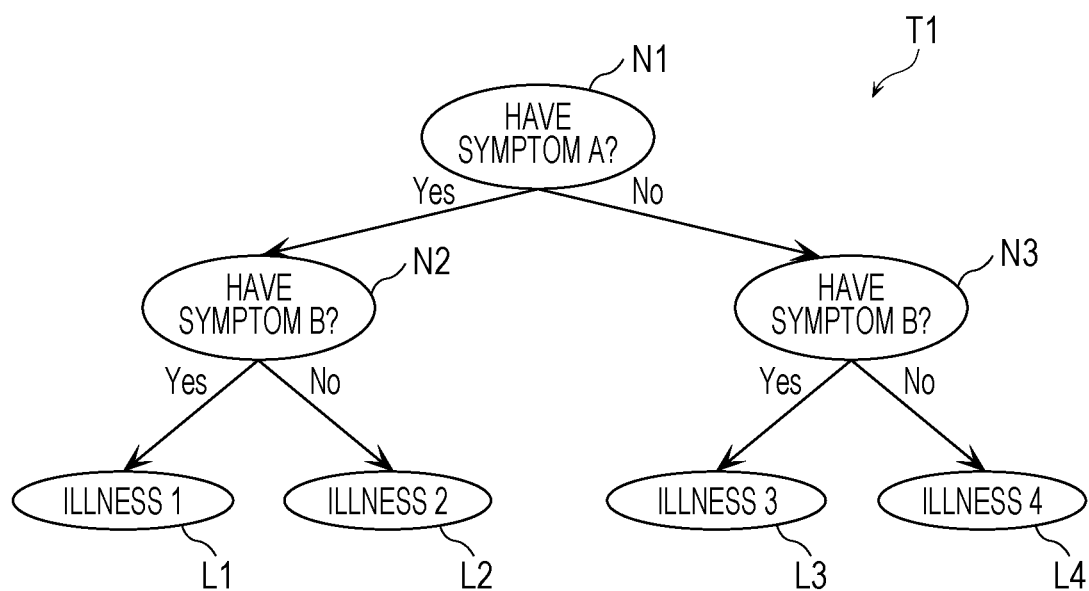
FIG. 4 illustrates a decision tree in the first embodiment.

FIG. 4 illustrates a decision tree T1 in the first embodiment. The decision tree T1 is an exemplary decision tree for identifying one of the plurality of illnesses illustrated in FIG. 3 through sequential questions. With the decision tree T1, it is possible to search for the illness of a user among illnesses 1 to 4 on the basis of user's answers to two questions as to whether or not the user is exhibiting the symptom A and whether or not the user is exhibiting the symptom B.

It should be noted that the decision tree for identifying one of the plurality of illnesses illustrated in FIG. 3 is not limited to the decision tree T1 illustrated in FIG. 4 and may be another decision tree. Various studies have been done on the related art on how to create a decision tree for identifying each of a plurality of illnesses by using as few questions as possible. This embodiment may be implemented by using any type of decision tree.

The decision tree T1 illustrated in FIG. 4 has a data structure in the form of a tree including nodes N1, N2, and N3 and leaves L1, L2, L3, and L4. Each of the nodes N1, N2, and N3 is associated with a corresponding one or more questions for identifying one or more pieces of information including one of the plurality of predetermined illnesses. In addition, each of the leaves L1, L2, L3, and L4 is associated with a corresponding one of the plurality of predetermined illnesses.

The task processing unit 26 focuses on the nodes one by one from a root node (node N1) toward the leaves in the decision tree T1. The focused node is also referred to as a node of attention.

The task processing unit 26 presents a question corresponding to a node of attention to the user and acquires the user's answer to the presented question. Among child nodes of the node of attention, the task processing unit 26 sets a child node corresponding to the answer acquired from the user as a new node of attention and presents a question corresponding to the node of attention to the user. Upon reaching one of the leaves by repeating this process, the task processing unit 26 identifies the illness corresponding to the leaf as the illness of the user.

Specifically, by using the decision tree T1, with respect to the question as to whether the user is exhibiting the symptom A (node N1), in principle, the task processing unit 26 acquires an answer indicating that the symptom A is exhibited, i.e., an affirmative answer (Yes), or an answer indicating that the symptom A is not exhibited, i.e., a negative answer (No). Then, with respect to the question as to whether the user is exhibiting the symptom B (node N2 or N3), the task processing unit 26 acquires an answer indicating Yes or No. In the above manner, the task processing unit 26 identifies the illness of the user from among the illnesses 1 to 4 through a search.

It should be noted that in the decision tree T1, (a) among child nodes of each of the nodes contained in the decision tree T1, each child node corresponding to the next question to be presented if an affirmative answer to the question corresponding to the node is acquired, may be arranged in a predetermined direction with respect to the node, and (b) among child nodes of each of the nodes contained in the decision tree T1, each child node corresponding to the next question to be presented if a negative answer to the question corresponding to the node is acquired, may be arranged in a direction different from the predetermined direction with respect to the node. That is, in the decision tree T1, the task processing unit 26 may arrange a child node in the lower left of a single node, the child node corresponding to the next question to be presented if an answer indicating Yes to a question corresponding to the single node is acquired, and may arrange a child node in the lower right of the single node, the child node corresponding to the next question to be presented if an answer indicating No to the question is acquired. With such arrangement, the user who has seen this decision tree can intuitively grasp how the question and answers to this question are connected to each other in the decision tree.

Figure 5:
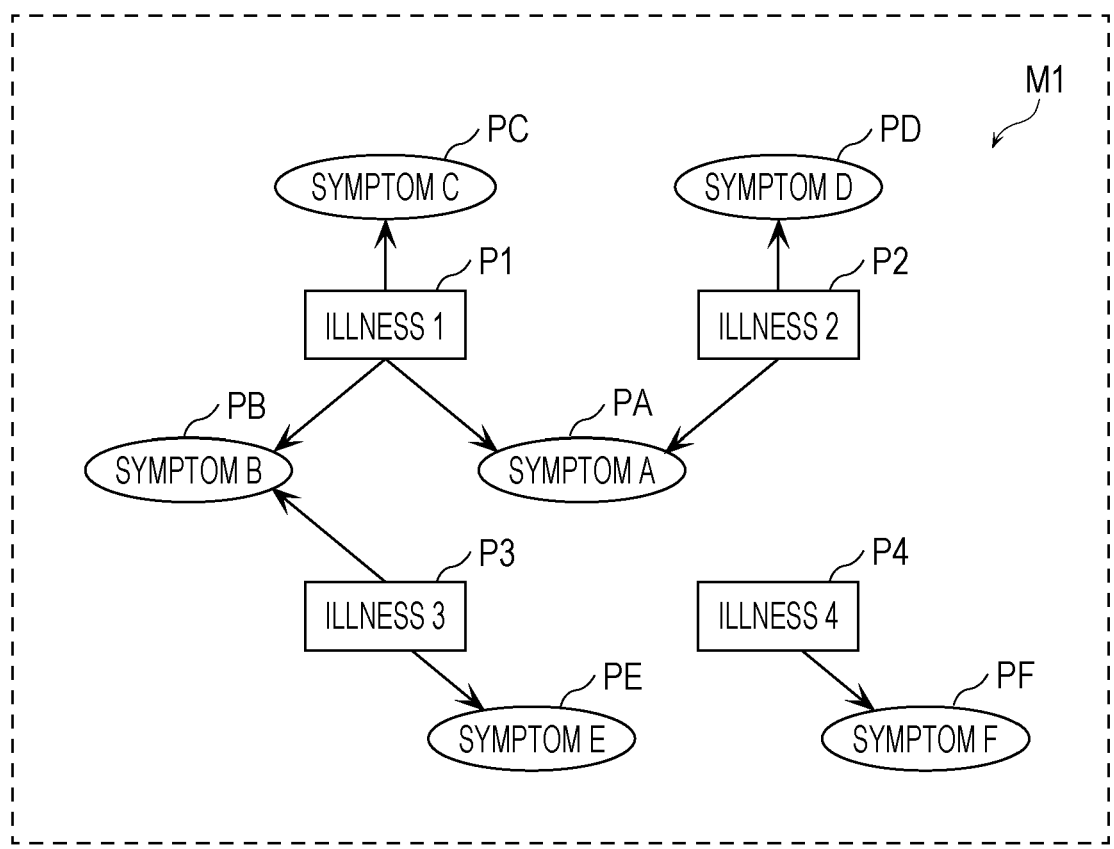
FIG. 5 illustrates a network in the first embodiment.

FIG. 5 illustrates a network M1 in this embodiment.

As illustrated in FIG. 5, the network M1 includes nodes P1 to P4 and nodes PA to PF. Each of the nodes P1 to P4 corresponds to a corresponding one of a plurality of predetermined illnesses, each of the nodes PA to PF corresponds to a corresponding one of symptoms that a person having a predetermined illness exhibits and is connected to one or more nodes corresponding to the predetermined illness that causes the symptoms (one or more nodes among the nodes P1 to P4). The network M1 thus configured may be referred to as a list of illnesses that cause the symptoms that the user is exhibiting and symptoms of the respective illnesses on the basis of the information on the symptoms having been acquired from the user through interactions up to this time point.

Figure 6:
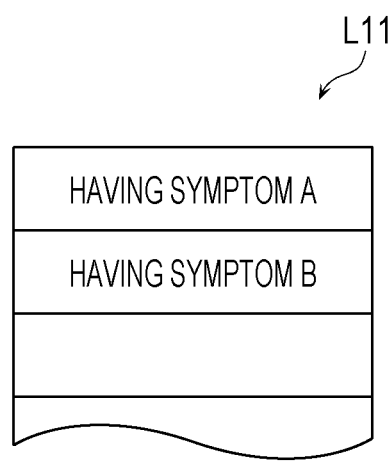
FIG. 6 illustrates a keyword list in the first embodiment.

FIG. 6 illustrates a keyword list L11 in this embodiment.

The keyword list L11 illustrated in FIG. 6 is a list in which information based on the user's answers is registered as keywords, the list being stored in the storage unit 28. Data in the keyword list L11 is cleared prior to initiating interactions between the search support apparatus 10 and the user. Then, keywords are registered in the keyword list L11 on the basis of answers acquired by the search support apparatus 10 from the user through interactions with the user. Specifically, text data acquired by the task processing unit 26 from the classification unit 24 is registered in the keyword list L11.

The keyword list L11 illustrated in FIG. 6 illustrates a keyword list obtained when, after an answer indicating "having symptom A" has been acquired from the user, an answer indicating that the user is exhibiting the symptom B is further acquired. The keyword list L11 is a list in which symptoms that the user is exhibiting and symptoms that the user is not exhibiting are sorted according to the user's answers, and registration of keywords in the keyword list L11 corresponds to transition of the node of attention from the root node toward the leaves in the decision tree.

It should be noted that, in the case where an answer indicating "Yes" has been acquired from the user to the presented question, the answer is handled as an answer affirming the presented question. That is, in the case where an answer indicating "Yes" is acquired from the user to the question "Do you have a symptom A?", a keyword "HAVING SYMPTOM A" is registered in the keyword list L11.

Figure 7:
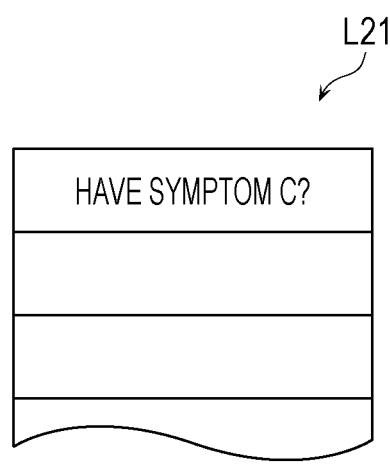
FIG. 7 illustrates an exclusion list in the first embodiment.

FIG. 7 illustrates an exclusion list L21 in this embodiment.

The exclusion list L21 illustrated in FIG. 7 is a list in which items are registered, the items being excluded from the items to be asked to the user, and is stored in the storage unit 28. Data in the exclusion list L21 is cleared prior to initiating interactions between the search support apparatus 10 and the user. Then, keywords are registered in the exclusion list L21 on the basis of answers acquired by the search support apparatus 10 from the user through interactions with the user. Specifically, the presented question is registered in the exclusion list L21 in the case where an answer from the user is included in neither candidate answers to the presented question nor candidate answers to other questions in the decision tree. Specifically, a keyword decided by the task processing unit 26 on the basis of the above-described condition is registered in the exclusion list L21. The exclusion list L21 is used at the time of reconstruction of the decision tree.

A process in a search support method executed by the search support apparatus 10 configured in the above manner will be described below.

Figure 8A:
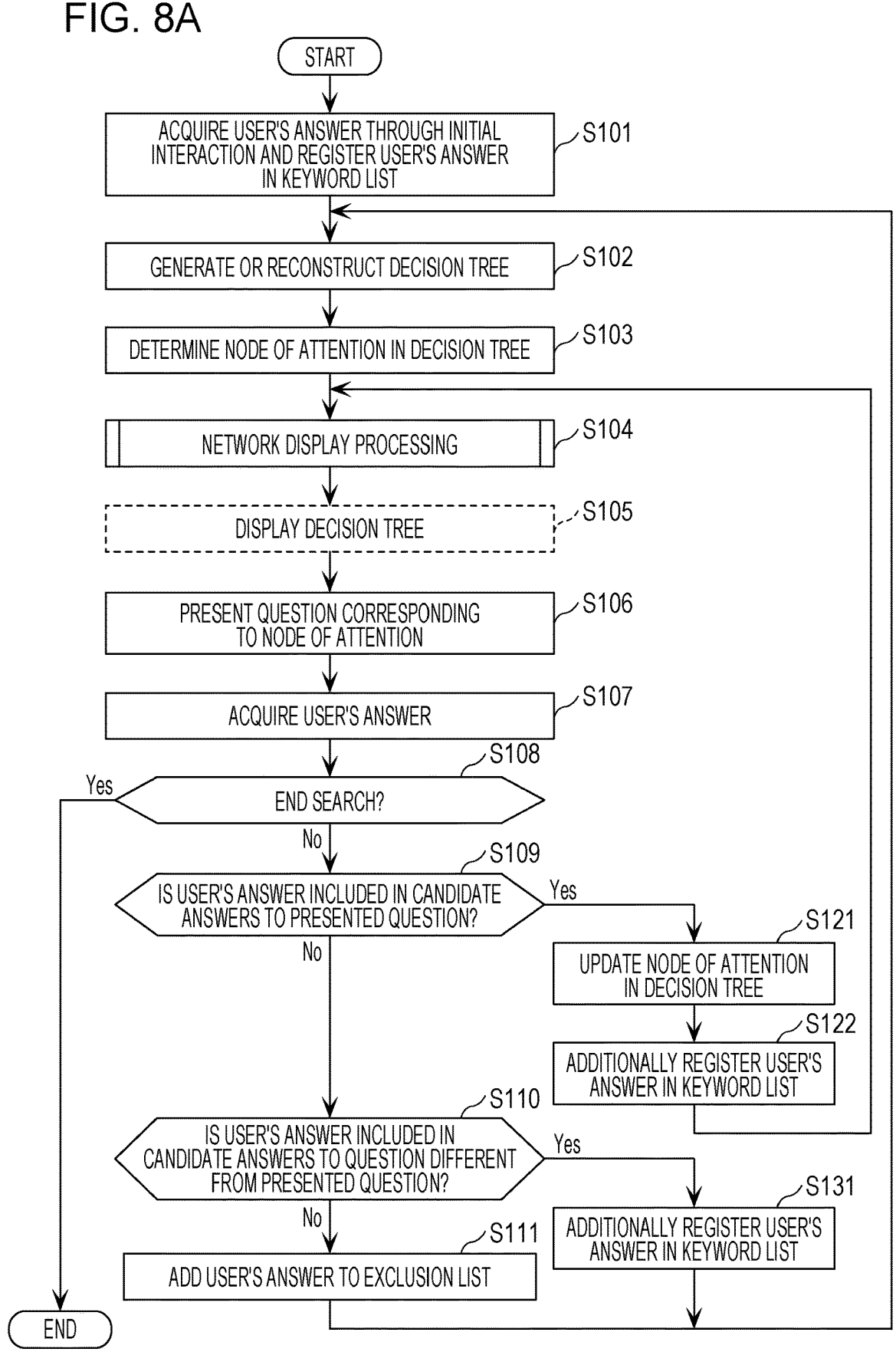
FIG. 8A is a flowchart illustrating a process flow in a search support method according to the first embodiment.
Figure 8B:
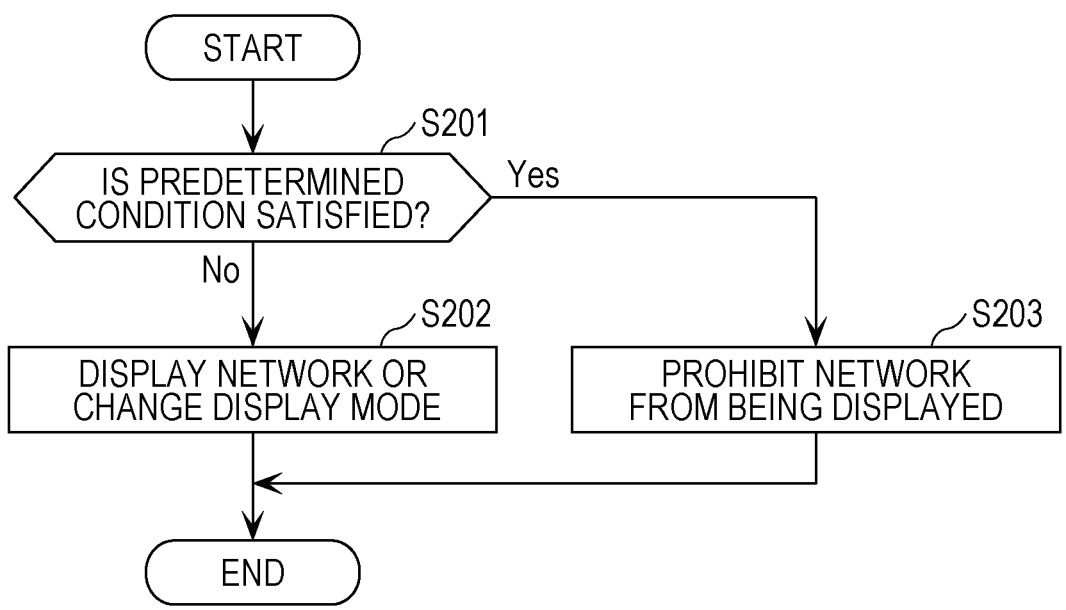
FIG. 8B is a flowchart illustrating a flow of network display processing in the search support method according to the first embodiment.

FIG. 8A is a flowchart illustrating a process flow in the search support method according to this embodiment. FIG. 8B is a flowchart illustrating a flow of network display processing in the search support method according to the first embodiment. The search support method executed by the search support apparatus 10 will be described with reference to FIGS. 8A and 8B.

Prior to performing a series of processing steps illustrated in FIG. 8A, the search support apparatus 10 clears data in a keyword list stored in the storage unit 28. That is, at the time point of performing step S101, not a single keyword is registered in the keyword list.

In step S101, the task processing unit 26 performs an initial interaction with the user to acquire information on symptoms that the user is exhibiting to register the acquired information on the symptoms in a keyword list as keywords. The initial interaction means an interaction including the initial question that asks about symptoms that the user is exhibiting and a user's answer to the question. Through the initial interaction, the task processing unit 26 acquires information on one or more symptoms among the symptoms that the user is exhibiting. The task processing unit 26 acquires the information on one or more symptoms by, for example, receiving, by using the microphone 20, the words that the user has uttered by being asked about the symptoms exhibited, performing speech recognition by using the speech recognition unit 22, and by performing meaning classification by using the classification unit 24.

In step S102, the task processing unit 26 generates a decision tree on the basis of the initial keyword acquired in step S101. Various methods are possible as a method for generating the decision tree. One of the methods will be described below.

First, the task processing unit 26 generates, as a root node of the decision tree, a node corresponding to a question as to whether or not the user is exhibiting the symptom indicated by the initial keyword acquired in step S101.

Then, from among the pieces of data on illnesses that are kept in advance, the task processing unit 26 extracts data on all illnesses that cause the symptom corresponding to the keyword acquired in step S101 and selects one of the symptoms that are caused by about half the extracted illnesses. Then, the task processing unit 26 generates, as a child node of the root node, a node corresponding to a question as to whether or not the user is exhibiting the selected one of the symptoms. The child node of the root node is only this node. Candidate answers to this question are Yes (i.e., exhibiting the symptom) and No (i.e., not exhibiting the symptom). It should be noted that, at the time of selecting one of the symptoms, if there are a plurality of symptoms that are caused by about half the extracted one or more illnesses, an arbitrary one of the plurality of symptoms (e.g., the first one in the plurality of symptoms arranged in a predetermined order) is selected.

Then, from among the pieces of data on illnesses that are kept in advance, the task processing unit 26 extracts data on all illnesses that cause the symptom related to the question corresponding to the above-described child node and data on all illnesses that do not cause the symptom and performs the above-described process on the extracted data on the one or more illnesses, thereby generating child nodes of the child nodes (i.e., grandchild nodes of the root node). Child nodes are generated one by one in this manner, and when there is one illness that causes a symptom related to a question, a leaf corresponding to this illness is generated. Even if a node corresponds to two or more illnesses, if it is not possible to find a question that divides the illnesses into two groups: a group of illnesses that causes a symptom related to the question and a group of illnesses that do not cause the symptom, this node is set as a leaf without generating a child node.

With this method, a decision tree including, as leaves, all illnesses that cause the symptom corresponding to the keyword acquired in step S101 is generated.

It should be noted that in the case where step S102 is performed after performing step S111 or S131, which will be described later, a keyword in an exclusion list may have been registered in some cases. In this case, at the time of generating child nodes, by selecting a question corresponding to a child node from among questions excluding a question registered in the exclusion list, a new decision tree is generated.

In step S103, the task processing unit 26 decides a node of attention in the decision tree. In the case where this step is performed for the first time after the acquisition of the keyword in step S101, the one child node of the root node is set as the node of attention.

In step S104, the task processing unit 26 performs network display processing. The network display processing is processing for displaying or not displaying a network (e.g., the network M1 in FIG. 5) on the display device 36. Details of the network display processing will be described later.

In step S105, the task processing unit 26 causes the display device 36 to display the decision tree generated in step S102 in a predetermined display mode under control of the display control unit 34. In addition, in the case where the task processing unit 26 has already caused the display device 36 to display the decision tree, the task processing unit 26 changes the display mode of the displayed decision tree to a predetermined display mode. It should be noted that step S105 is not a necessary processing step and may not be necessarily performed.

It should be noted that in the case where the display device 36 is caused to display the decision tree in step S105, the display device 36 may display an image in which the network displayed in step S104 and the decision tree are arranged side by side. In this case, the user can see the decision tree and the network at a certain time point together on a single screen.

In step S106, the task processing unit 26 presents a question corresponding to the node of attention to the user. Although various methods may be possible to present the question, there is a method of, for example, outputting text data of the question as speech by using the speech synthesis unit 30 and the speaker 32. It should be noted that the question may be presented to the user with the decision tree generated in step S102 displayed on the display device 36.

In this case, the user can answer the presented question by grasping the position thereof in a series of questions.

In step S107, the task processing unit 26 acquires a user's answer. The microphone 20 receives the words uttered by the user after the question has been presented to the user in step S106, the speech recognition unit 22 recognizes the speech, and the classification unit 24 classifies the meaning, whereby the user's answer is acquired. It should be noted that the answer acquired by the task processing unit 26 in step S107 may include an affirmative answer and negative answer to the question presented to the user in step S106 and affirmative answers to other questions excluding the question presented in step S106 from the questions included in the decision tree. By allowing the affirmative answers to the other questions to be acquired, the other questions excluding the question presented in step S106 from the questions included in the decision tree, the degree of freedom of the interactions is increased.

It should be noted that in the case where it is not possible to acquire a user's answer even when a predetermined period passes after the question has been presented to the user in step S106, the process proceeds on the assumption that an answer indicating that there is no valid answer to the question has been acquired.

In step S108, on the basis of the user's answer acquired in step S107, the task processing unit 26 determines whether or not the information search is to end. Specifically, on the basis of the user's answer acquired in step S107, the task processing unit 26 performs the determination by determining whether or not the process has reached a leaf, that is, whether or not there are no more questions in the decision tree. If there are no more questions, it is determined that the information search is to end. If it is determined in step S108 that the information search is to end (Yes in step S108), the series of processing steps end. On the other hand, if it is determined in step S108 that the search for information is not to end (No in step S108), the process proceeds to step S109.

In step S109, the task processing unit 26 determines whether or not the user's answer acquired in step S107 is included in the candidate answers to the question presented in step S106. If it is determined that the user's answer acquired in step S107 is included in the candidate answers to the question (Yes in step S109), the process proceeds to step S121. On the other hand, if it is determined that the user's answer acquired in step S107 is not included in the candidate answers to the question (No in step S109), the process proceeds to step S110. It should be noted that in the case where an answer indicating that there is no valid answer to the question has been acquired in step S107, it is determined that the user's answer acquired in step S107 is not included in the candidate answers to the question.

In step S110, the task processing unit 26 determines whether or not the user's answer acquired in step S107 is included in the candidate answers to the other questions excluding the question presented in step S106 from the questions included in the decision tree. If it is determined in step S110 that the user's answer is included in the candidate answers to the other questions (Yes in step S110), the process proceeds to step S131. On the other hand, if it is determined in step S110 that the user's answer is not included in the candidate answers to the other questions (No in step S110), the process proceeds to step S111.

In step S111, the task processing unit 26 registers the question presented in step S106 in the exclusion list. Then, the process proceeds to step S102.

In step S121, the task processing unit 26 updates the node of attention in the decision tree. Specifically, the task processing unit 26 updates the node of attention in such a manner that, among child nodes of the node of attention at the current time point, a child node corresponding to the answer acquired in step S107 is set as a new node of attention.

In step S122, the task processing unit 26 registers the user's answer acquired in step S107 in the keyword list. Then, the process proceeds to step S104.

In step S131, the task processing unit 26 registers the user's answer acquired in step S107 to the keyword list. Then, the process proceeds to step S102.

Next, the network display processing in step S104 will be specifically described with reference to FIG. 8B.

In step S201, the task processing unit 26 determines whether or not a predetermined condition based on an interaction situation is satisfied. The predetermined condition indicates a condition for prohibiting the display of the network. The predetermined condition can be, for example, a condition such that the sum of the number of a plurality of illnesses that are considered to be an illness of the user on the basis of keywords (the presence and absence of symptoms) obtained through interactions up to the current time point and the number of symptoms of the plurality of illnesses exceeds a predetermined number. It should be noted that the predetermined number is defined as the number of nodes displayed altogether on the display device 36, the number of nodes being noticeable by a person at a time, and can be, for example, about 20 or 30.

In step S202, the task processing unit 26 causes the display device 36 to display a network. If the task processing unit 26 has already caused the display device 36 to display the network, the task processing unit 26 changes the display mode of the displayed network. More specifically, for example, the display mode of a node corresponding to a question for which an answer has been acquired from the user to a predetermined display mode indicating that the search has been progressed.

In step S203, the task processing unit 26 prohibits the display device 36 from displaying the network.

Through the above-described series of processing steps, the search support apparatus 10 progresses the search while causing the display device 36 to display the network and changing the display mode of the displayed network. In particular, by causing the display device 36 to display the network, it is possible to present a plurality of symptoms to the user at a time on the basis of the keyword list. With the plurality of symptoms presented, the user easily answers the symptoms exhibited from among the plurality of presented symptoms. That is, the user easily answers a symptom that is different from the symptom related to the question presented in step S106. An answer different from any of the candidate answers to the presented question about a symptom, the answer being provided on the basis of the presented information, encourages reconstruction of the decision tree (Yes in step S110, step S131, and step S102). Thus, the illness of the user can be quickly identified. In the above manner, the search support apparatus 10 can suppress the user's feeling of anxiety or irksomeness at the time of engaging in questions and answers in search of desired information.

Operations of the search support apparatus 10 will be described below with reference to two specific examples of interactions. A first interaction example corresponds to an exemplary case where the search support apparatus 10 searches for information by using a decision tree (this case may also be hereinafter referred to as a comparative example). A second interaction example corresponds to an exemplary case where the search support apparatus 10 searches for information by presenting a network at a certain time point and acquiring a user's answer based on the presented network.

Figure 9:
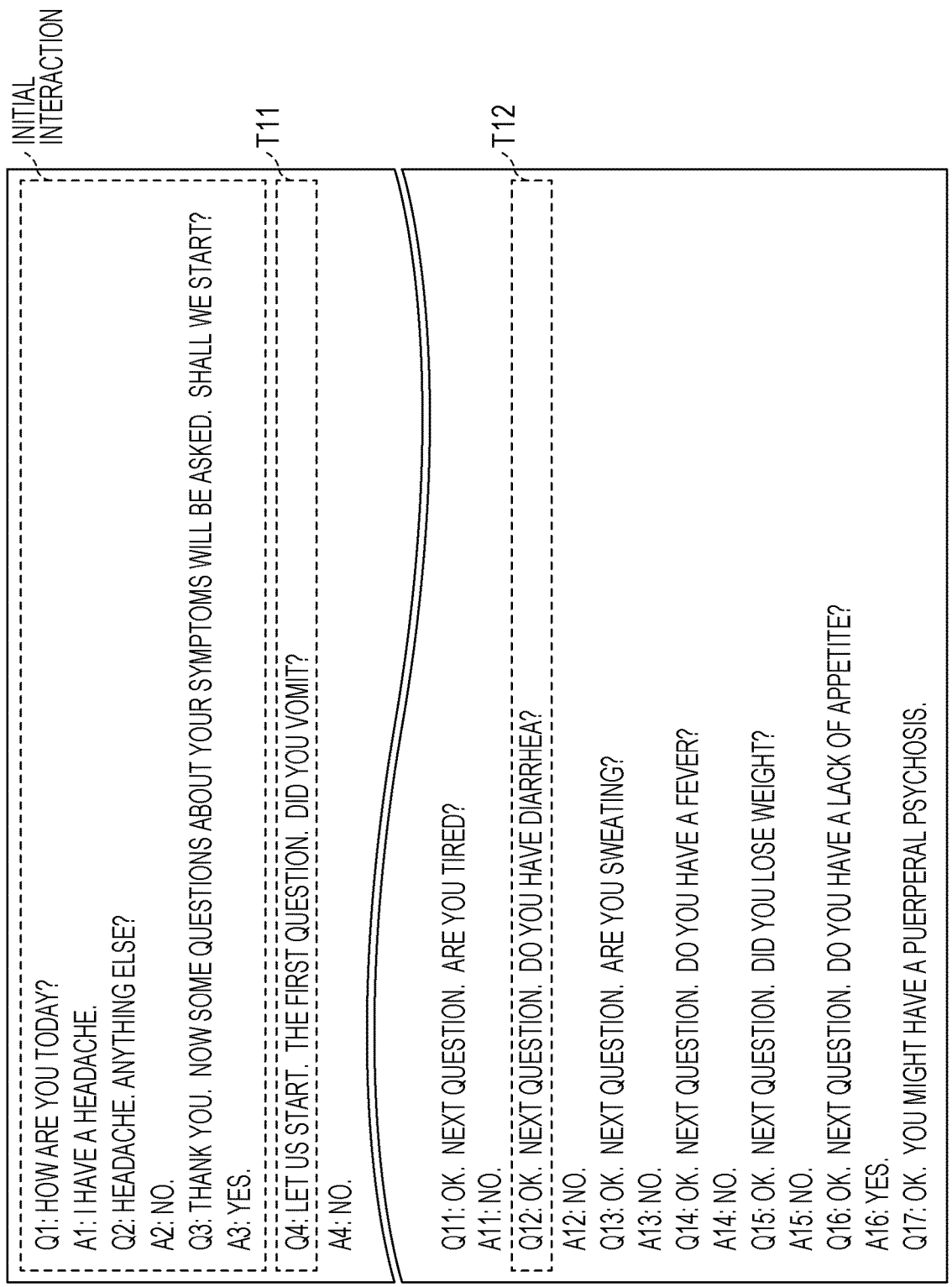
FIG. 9 illustrates a comparative example of interactions in the first embodiment.

FIG. 9 illustrates the comparative example of interactions in this embodiment. The comparative example of interactions illustrated in FIG. 9 indicates contents of interactions through which a user exhibiting certain symptoms identifies the illness that causes the symptoms by using the search support apparatus 10. It should be noted that FIG. 9 illustrates the contents of speech made by the search support apparatus 10 as "Q (questioner)" and the contents of speech made by the user as "A (respondent)". A decision tree and a keyword list obtained at time points T11 and T12 in this series of interactions will be described.

First, the search support apparatus 10 attempts to acquire symptoms that the user is exhibiting through an initial interaction (speeches Q1 to A3).

In the initial interaction, the search support apparatus 10 asks about the symptoms that the user is exhibiting by saying "HOW ARE YOU TODAY?" to the user (speech Q1). The user provides an answer to the question, the answer indicating that the user has a headache, "I HAVE A HEADACHE" (speech A1). On the basis of the user's answer, the search support apparatus 10 registers a keyword indicating that the user has a headache, specifically "HAVING HEADACHE", in a keyword list (step S101). After asking the user if the user has other symptoms, the search support apparatus 10 ends the initial interaction (speech Q2 to A3).

Upon completion of the initial interaction, on the basis of information on the user's symptom acquired through the initial interaction, that is, the keyword registered in the keyword list at this time, the search support apparatus 10 generates a decision tree and decides a node of attention in the decision tree (steps S102 and S103).

Then, the search support apparatus 10 performs network display processing and also asks a first question, "DID YOU VOMIT?" (steps S104 to S106, speech Q4). This time point is set as the time point T11. On and after the time point T11, interactions are continued between the search support apparatus 10 and the user (speech Q11 to A16). In the interactions with the user, a time point at which the predetermined condition for prohibiting the display of the network is no longer satisfied is set as the time point T12.

Figure 10:
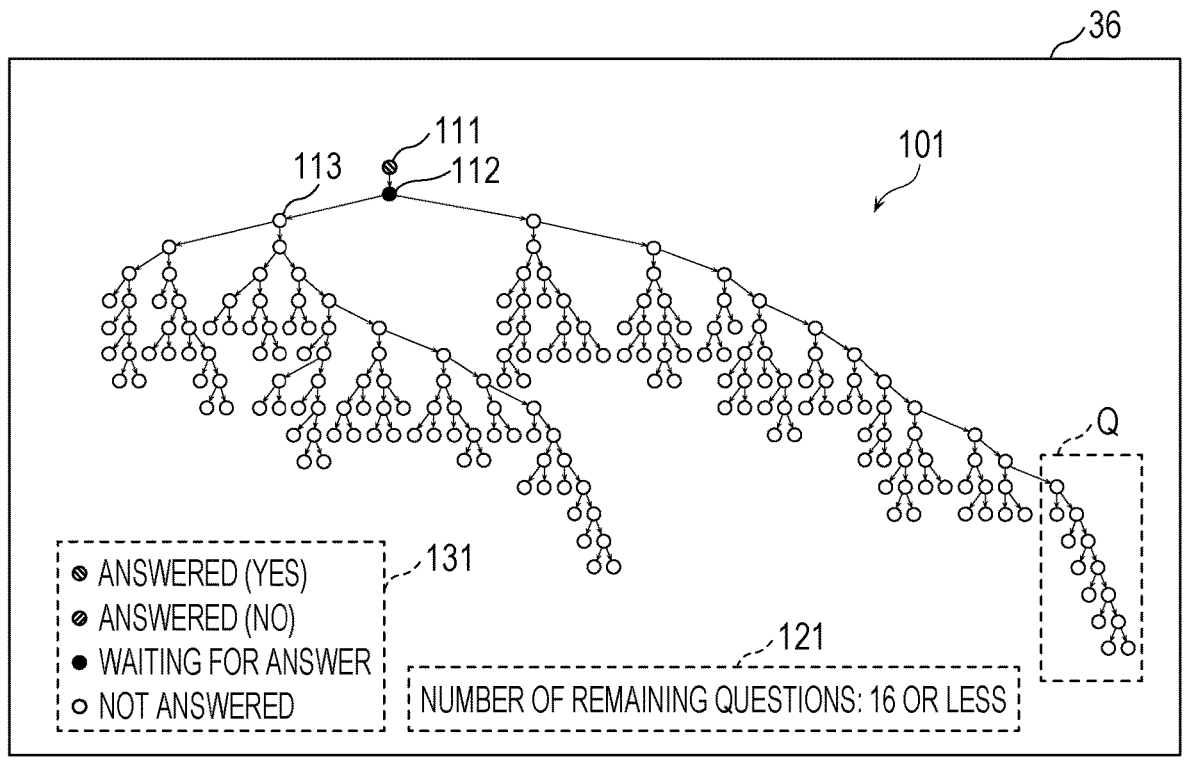
FIG. 10 illustrates a decision tree displayed on a display device at a first time point in the comparative example of interactions in the first embodiment.
Figure 11:
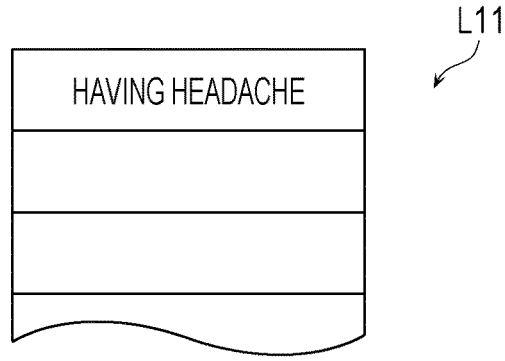
FIG. 11 illustrates a keyword list at the first time point in the comparative example of interactions in the first embodiment.

FIG. 10 illustrates a decision tree displayed on the display device 36 at the time point T11 in the comparative example. FIG. 11 illustrates a keyword list at the time point T11 in the comparative example.

As illustrated in FIG. 10, at the time point T11, the display control unit 34 causes the display device 36 to display a decision tree 101. A node 111 serving as a root node (the uppermost node in the figure) of the decision tree 101 is a node corresponding to a symptom of "having a headache". A node 112 is a node corresponding to a question that has been asked to the user and is waiting for an answer from the user, the node corresponding to a symptom of "having vomited". A node 113 is a node corresponding to a question yet to be presented to the user. In addition, the display control unit 34 causes the display device 36 to display a number of remaining questions 121 and explanatory notes 131 of display modes of the nodes.

In addition, as illustrated in FIG. 11, at the time point T11, "HAVING HEADACHE" is registered as a keyword in the keyword list L11. This is obtained from the user's answer (speech A2) in the initial interaction.

However, the above-described comparative example includes a part Q at which the efficiency of information search is low. This will be described below in detail.

Figure 12:
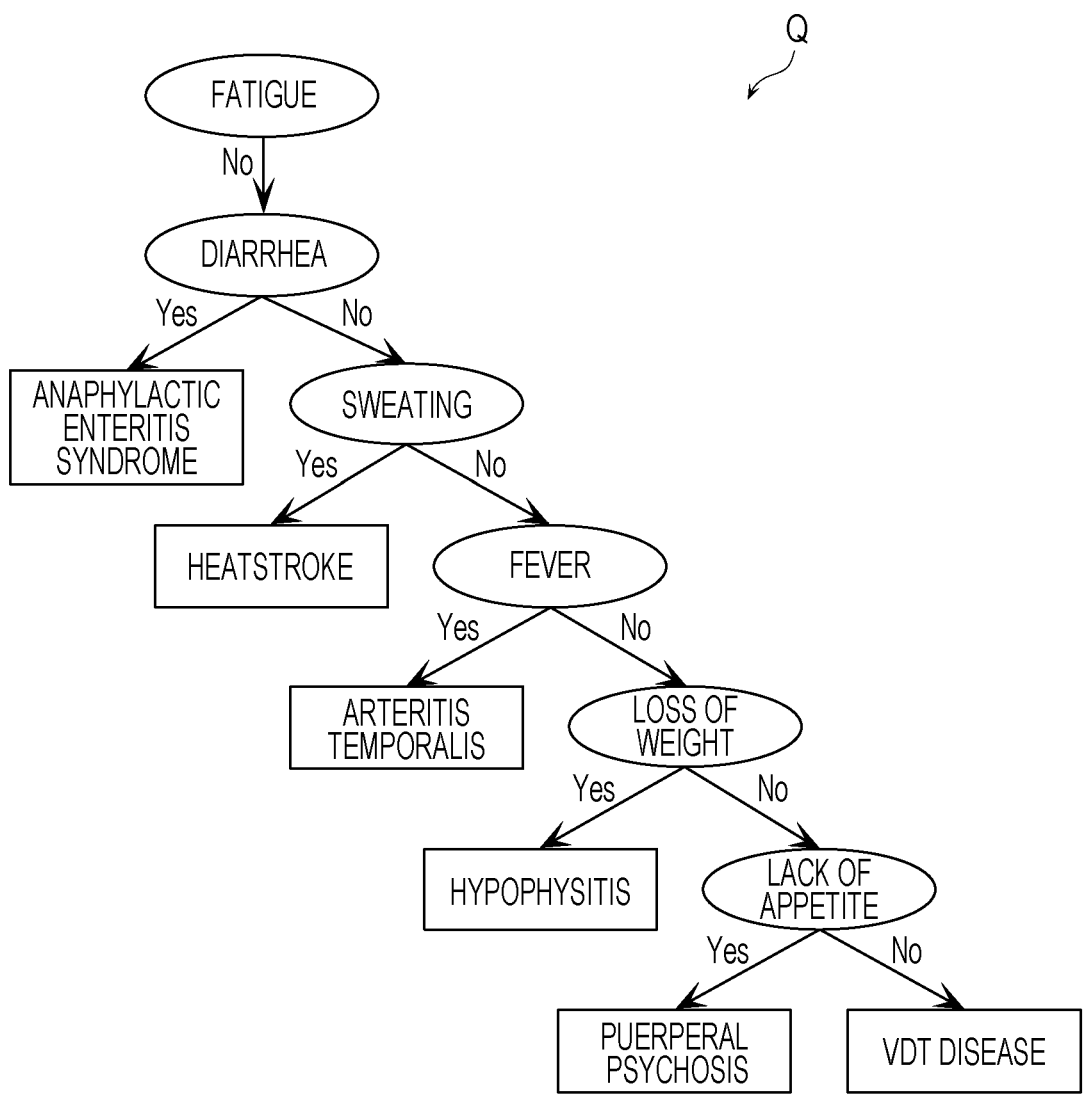
FIG. 12 illustrates a part of the decision tree at the first time point in the comparative example of interactions in the first embodiment.

FIG. 12 illustrates the part Q of the decision tree at the time point T12 in the comparative example of interactions in this embodiment. The decision tree illustrated in FIG. 12 illustrates the part Q illustrated in FIG. 10 including illnesses and symptoms corresponding to nodes.

As illustrated, in the part Q of the decision tree 101, the number of levels from the uppermost node to the lowermost leaf in the part Q is substantially equal to the number of leaves in the part Q. Accordingly, in the case where the search target is the leaf ("PUERPERAL PSYCHOSIS" or "VISUAL DISPLAY TERMINAL (VDT) DISEASE") that is the most distant from the uppermost node in the part Q, it is necessary to present a large number of questions to the user until the process reaches the leaf. That is, the user might feel anxious or irksome by being presented a large number of questions.

Specifically, for example, in the case where the user has a puerperal psychosis or VDT disease, the user is presented sequential questions as to whether symptoms of diarrhea, sweating, fever, loss of weight, and lack of appetite are exhibited (Q11 to Q15 in FIG. 9), and accordingly, the user might feel anxious or irksome.

In such a case, in the search support method executed by the search support apparatus 10 according to this embodiment, it is possible to suppress the user's feeling of anxiety or irksomeness.

Figure 13:
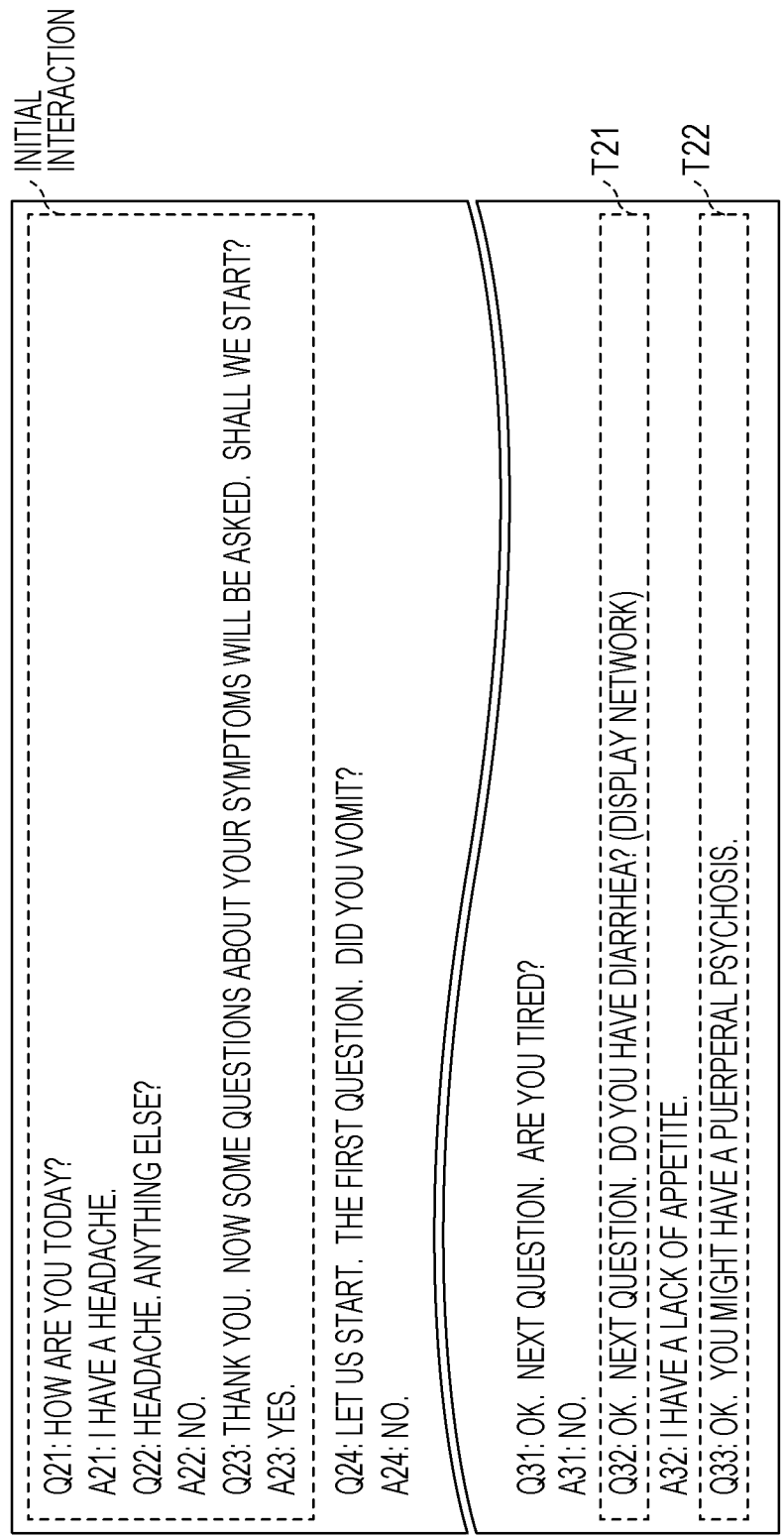
FIG. 13 illustrates a first interaction example made by the search support apparatus according to the first embodiment.

FIG. 13 illustrates a first interaction example made by the search support apparatus 10 according to this embodiment.

First, as in the comparative example (FIG. 9), the search support apparatus 10 attempts to acquire information on symptoms that the user is exhibiting through an initial interaction (step S101, speeches Q21 to A23).

Upon completion of the initial interaction, as in the case illustrated in FIG. 9, the search support apparatus 10 generates a decision tree and decides a node of attention in the decision tree (steps S102 and S103).

Then, the search support apparatus 10 displays the decision tree and also asks a first question, "DID YOU VOMIT?" (steps S104 to S106, speech Q24). On and after this time point, interactions are continued between the search support apparatus 10 and the user.

At a certain time point during the progress of interactions, the sum of the number of a plurality of illnesses that are considered to be an illness of the user on the basis of keywords (the presence and absence of symptoms) obtained through interactions up to this time point and the number of symptoms of the plurality of illnesses becomes less than or equal to a predetermined number. This time point is set as a time point T21.

Then, on the basis of the user's answers, the search support apparatus 10 identifies the illness of the user. This time point is set as a time point T22.

Figure 14A:
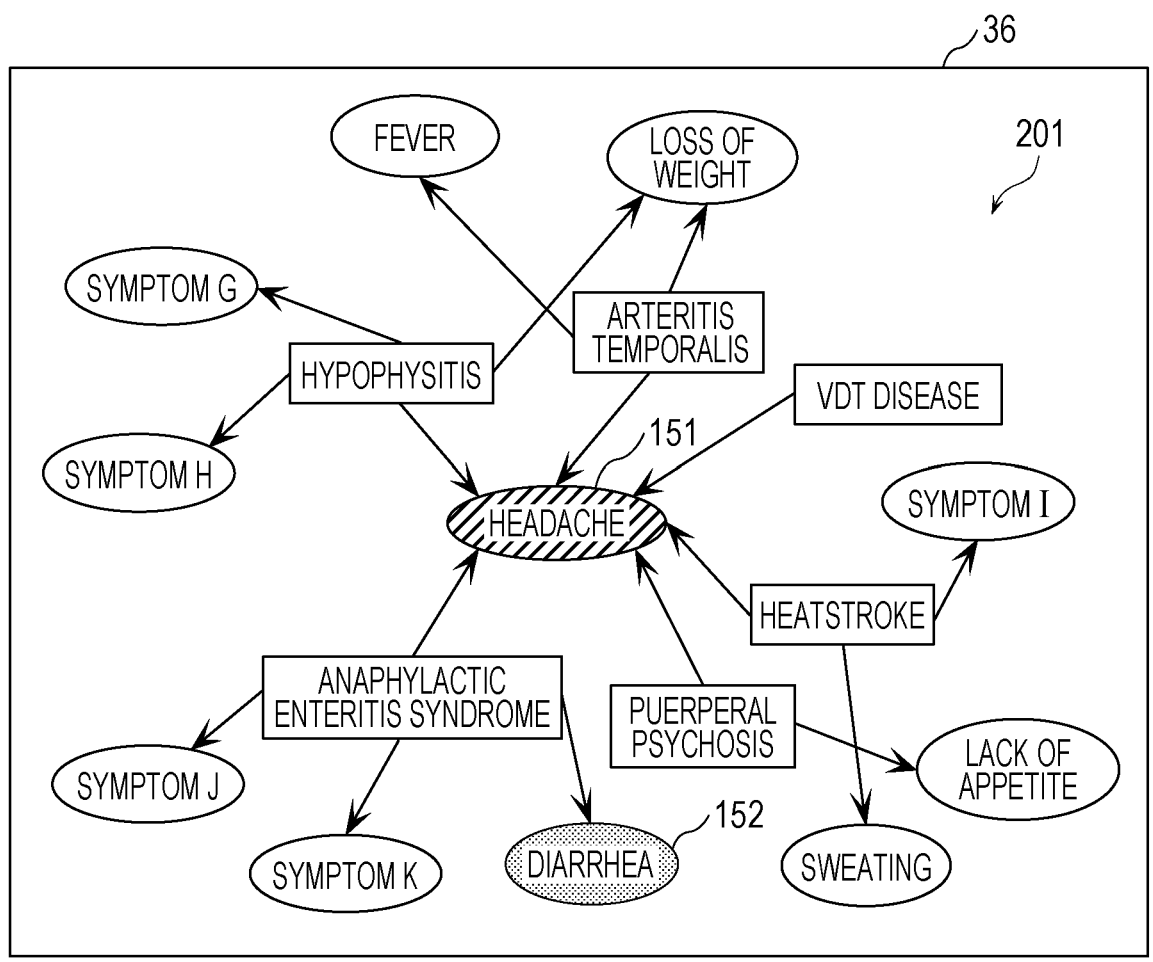
FIG. 14A illustrates a network displayed on a display device at a second time point in the first interaction example made by the search support apparatus according to the first embodiment.

FIG. 14A illustrates a network 201 displayed on the display device 36 at the time point T21 in the first interaction example made by the search support apparatus 10 according to this embodiment.

A node 151 corresponding to a symptom of a "headache" is arranged at the center of the network 201 illustrated in FIG. 14A. The node corresponding to the above symptom is connected to nodes corresponding to illnesses such as "hypophysitis" and "arteritis temporalis", which are illnesses causing the symptom of a "headache". In addition, the nodes corresponding to the above illnesses are connected to nodes corresponding to "fever" and "loss of weight", which are symptoms that a person having a corresponding illness exhibits.

At the current time point, a node 152 corresponding to the question being presented by the search support apparatus 10 is displayed in a display mode that is different from any of the display modes of the other nodes.

By seeing the network 201, the user can check whether symptoms among the nodes included in the network 201 are exhibited. If the network 201 includes the symptoms that the user is exhibiting, the user provides answers about symptoms to the search support apparatus 10. For example, if the user has a symptom of the lack of appetite, the user can provide an answer, "I HAVE A LACK OF APPETITE" (speech A32).

Upon acquiring the user's answer, the search support apparatus 10 determines that, although this answer is not included in candidate answers to the question that has been presented to the user, "DO YOU HAVE DIARRHEA?" (speech Q32), this answer is included in candidate answers to a question different from the question that has been presented (No in step S109, Yes in step S110). Accordingly, the search support apparatus 10 registers this answer in the keyword list to reconstruct the decision tree, decides the node of attention, and performs network display processing.

It should be noted that nodes corresponding to illnesses may not be displayed (the display may be prohibited) when the network is displayed. In other words, in the case where the search support apparatus 10 is connected to a first display device and a second display device, the first display device serving as a display device that displays information for a service provider that provides an information search service, the second display device serving as a display device that displays information for a service user who uses the information search service, nodes corresponding to illnesses may be allowed to be displayed on the first display device and may be prohibited from being displayed on the second display device when a network is displayed. Once seeing the names of illnesses, the user knows the illness that is to be identified if the symptoms exhibited are correctly answered and might not provide correct answers about the symptoms. By prohibiting the nodes from being displayed in the above manner, it is possible to encourage the user to provide correct answers about the symptoms.

Figure 14B:
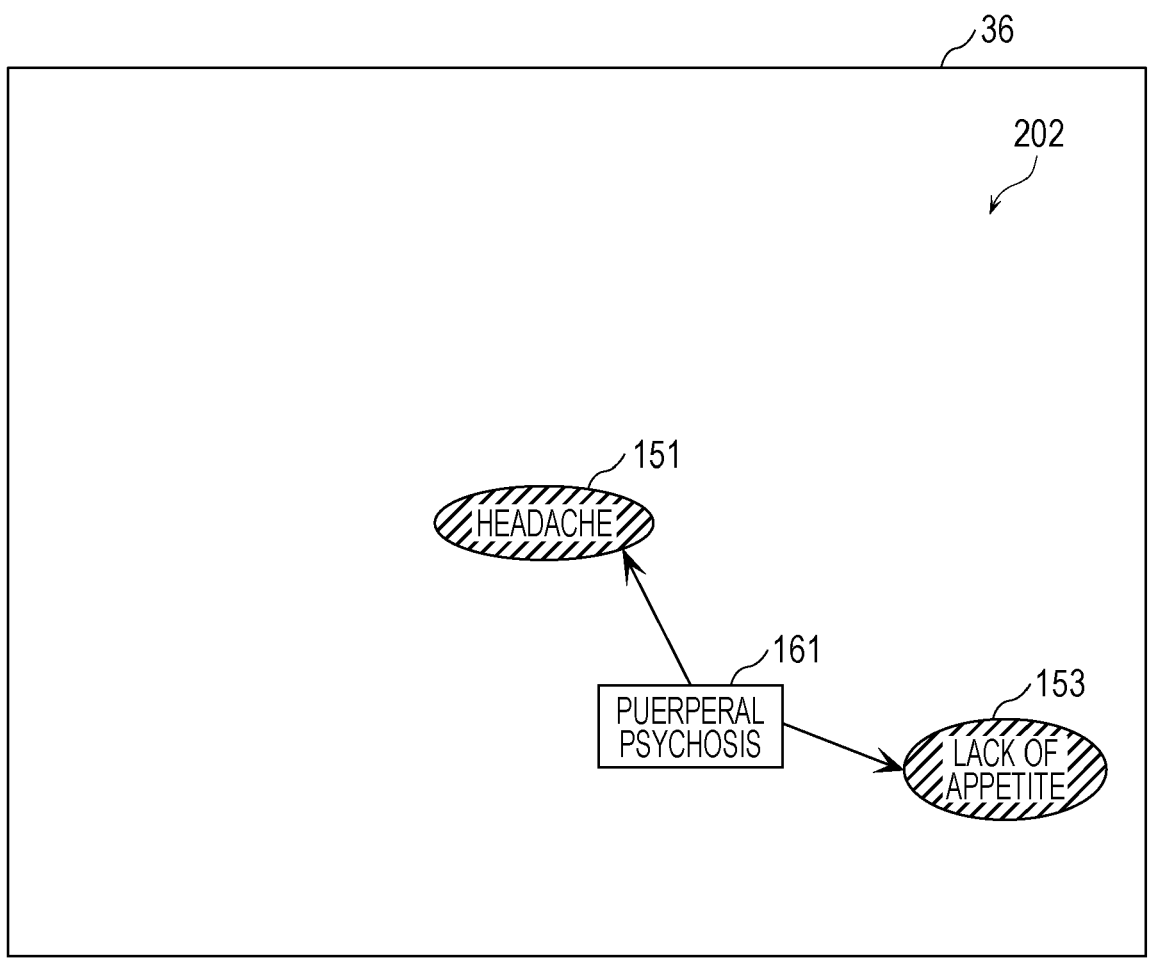
FIG. 14B illustrates a network displayed on a display device at a third time point in the first interaction example made by the search support apparatus according to the first embodiment.

FIG. 14B illustrates a network 202 displayed on the display device 36 at the time point T22 in the first interaction example made by the search support apparatus 10 according to the first embodiment.

As illustrated in FIG. 14B, the network 202 includes only the node 151 corresponding to "HEADACHE" and a node 153 corresponding to "LACK OF APPETITE" as nodes corresponding to symptoms and only a node 161 corresponding to "PUERPERAL PSYCHOSIS" as a node corresponding to an illness. This is because all the nodes have been deleted except for nodes corresponding to the symptoms according to the user's answers that have been provided up to the current time point as the symptoms that the user is exhibiting and a node corresponding to an illness that causes these symptoms. In the case where a single illness is identified in the above manner, the search may end without acquiring a user's answer (step S107).

Figure 15:
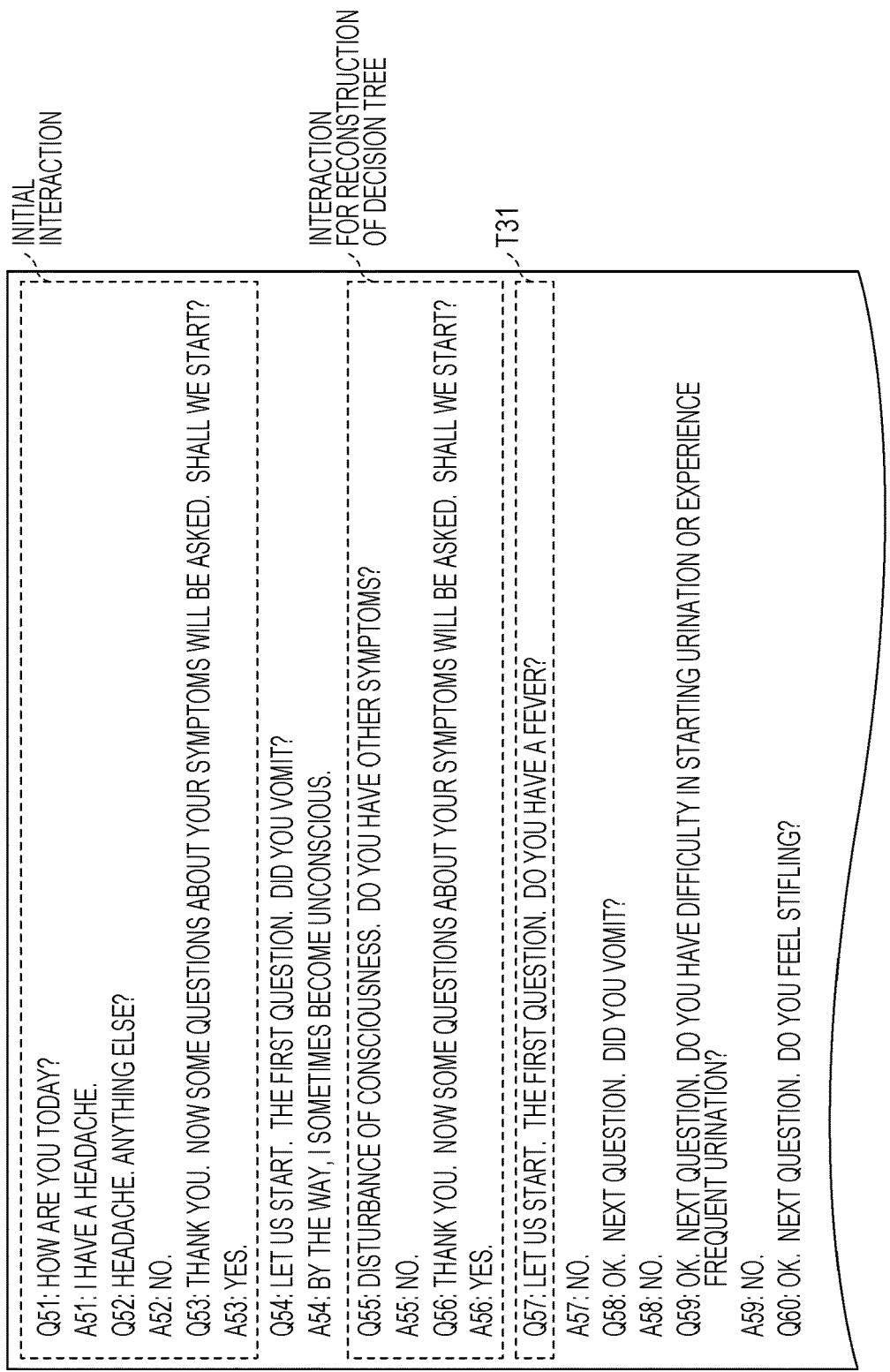
FIG. 15 illustrates a second interaction example made by the search support apparatus according to the first embodiment.

FIG. 15 illustrates a second interaction example made by the search support apparatus 10 according to this embodiment.

First, as in the comparative example (FIG. 9), the search support apparatus 10 attempts to acquire information on symptoms that the user is exhibiting through an initial interaction (step S101, speeches Q51 to A53).

Upon completion of the initial interaction, as in the case of the comparative example, the search support apparatus 10 generates a decision tree and decides a node of attention in the decision tree (steps S102 and S103).

Then, the search support apparatus 10 displays the decision tree and also asks a first question, "DID YOU VOMIT?" (steps S104 and S105, Q54). Expected candidate answers to this question is "Yes" indicating that the user vomited and "No" indicating that the user did not vomit.

In response, the user provides an answer, "I SOMETIMES BECOME UNCONSCIOUS", which is a different answer from any of the candidate answers (speech A54).

The task processing unit 26 determines that the above answer is not included in the candidate answers to the presented question (No in step S108), and then determines that the above answer is included in candidate answers to other questions excluding the presented question from the questions included in the decision tree (Yes in step S109). Then, the task processing unit 26 additionally registers the symptom "HAVING DISTURBANCE OF CONSCIOUSNESS" corresponding to the above answer in a keyword list (step S131), and, on the basis of the keyword list obtained after the registration, the task processing unit 26 reconstructs the decision tree and decides the node of attention in the decision tree (steps S102 and S103). This time point is a time point T31.

Figure 16:
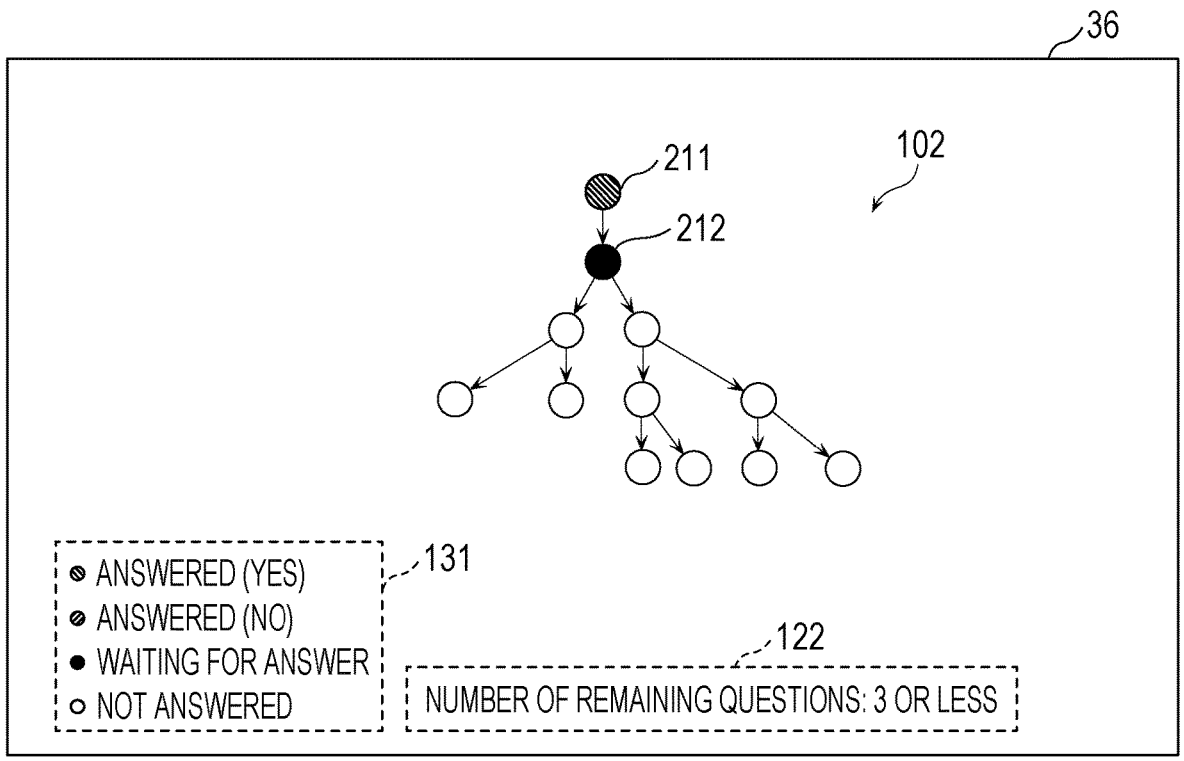
FIG. 16 illustrates a decision tree displayed at a second time point in the second interaction example made by the search support apparatus according to the first embodiment.
Figure 17:
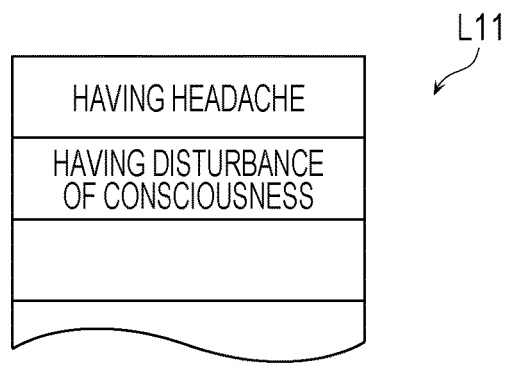
FIG. 17 illustrates a keyword list at the second time point in the second interaction example in the first embodiment.

FIG. 16 illustrates a decision tree displayed at the time point T31 in the second interaction example in this embodiment. FIG. 17 illustrates a keyword list at the time point T31 in the second interaction example in this embodiment.

As illustrated in FIG. 16, at the time point T31, the display control unit 34 causes the display device 36 to display a decision tree 102. A node 211 serving as a root node of the decision tree 102 is a node corresponding to a symptom of "having disturbance of consciousness". A node 212 is a node corresponding to a question that has been asked to the user and that is waiting for an answer from the user, the node corresponding to a symptom of "having a fever". In this manner, as a result of reconstruction of the decision tree, a decision tree is constructed in which information on the symptom registered in the keyword list at the time of reconstruction corresponds to the root node. In addition, a number of remaining questions 122 is updated on the basis of the reconstructed decision tree and the node of attention at the current time point.

In addition, as illustrated in FIG. 17, at the time point T31, "HAVING HEADACHE" and "HAVING DISTURBANCE OF CONSCIOUSNESS" are registered as keywords in the keyword list L11. These are obtained from the user's answers in the initial interaction and the following interactions.

Figure 18:
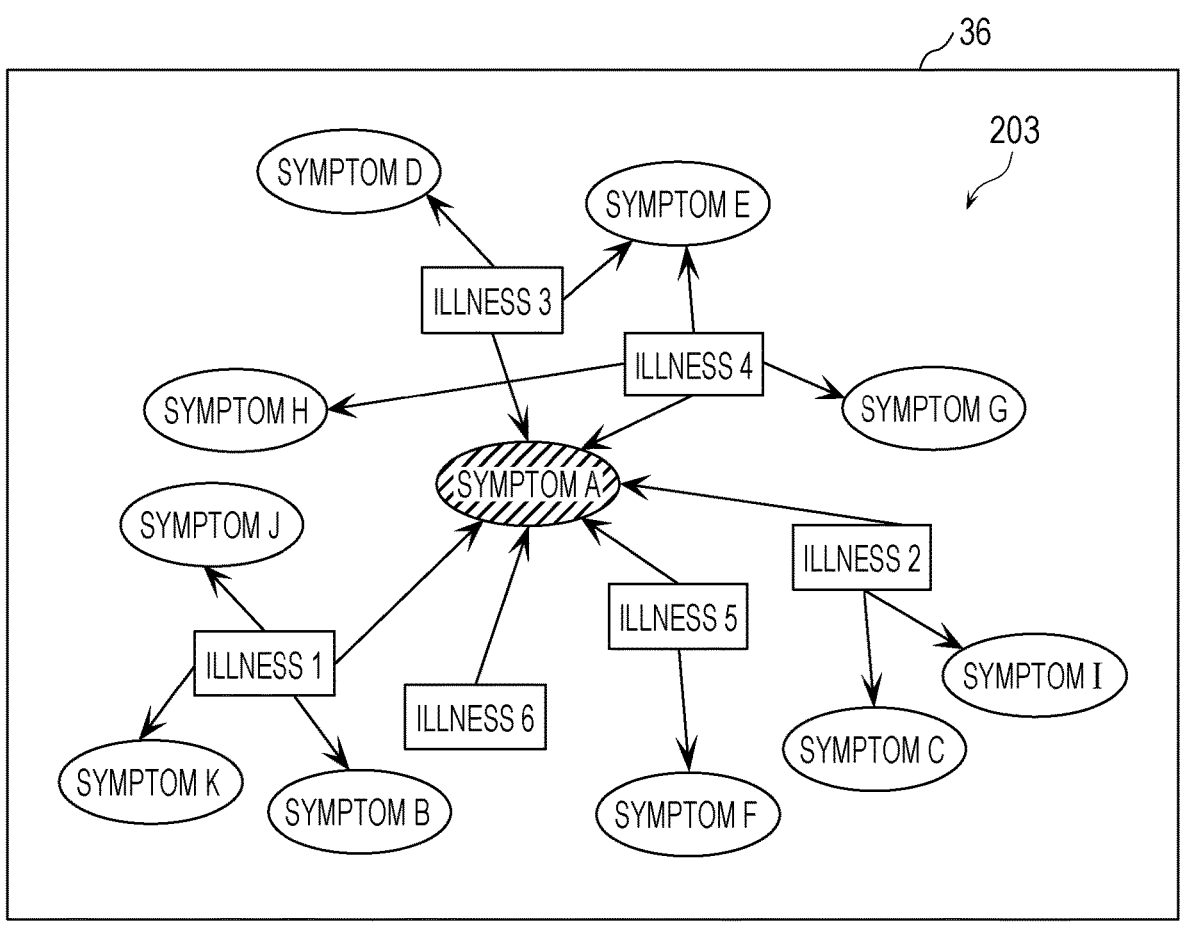
FIG. 18 illustrates a network displayed on a display device at the second time point in the second interaction example made by the search support apparatus according to the first embodiment.

FIG. 18 illustrates a network 203 displayed on the display device 36 at the time point T31 in the second interaction example made by the search support apparatus 10 according to this embodiment.

As illustrated in FIG. 18, the network 203 is obtained by changing the previous decision tree to a new one in accordance with the reconstruction of the decision tree. In this manner, the search support apparatus 10 updates the network 203 in accordance with the progress of the search by using the decision tree.

It should be noted that the case where the information handled by the search support apparatus 10 is information on illnesses and symptoms of illnesses has been described above. That is, in the above-described case, a plurality of pieces of predetermined information are a plurality of pieces of information indicating a plurality of predetermined illnesses, one piece of information is information indicating an illness of a user, and each of one or more nodes corresponds to a question as to whether or not the user is exhibiting a corresponding symptom caused by a corresponding one of the plurality of predetermined illnesses.

In addition, the search support apparatus 10 can handle the following information.

For example, the plurality of pieces of predetermined information may be a plurality of pieces of information indicating a plurality of real estate properties, the one piece of information may be information indicating a real estate property that the user desires, and each of the one or more nodes may correspond to a question as to whether or not the house rent of a corresponding real estate property, the distance from the nearest station, or the time it takes from the nearest station by walk satisfies desired conditions of the user.

In addition, the plurality of pieces of predetermined information may be a plurality of pieces of information indicating a plurality of itineraries, the one piece of information may be information indicating an itinerary that the user desires, and each of the one or more nodes may correspond to a question as to whether or not the purchase price of a corresponding itinerary, the destination, or the nights of stay satisfies desired conditions of the user.

Furthermore, the plurality of pieces of predetermined information may be a plurality of pieces of information indicating remedial measures for a plurality of fault conditions that may occur in a predetermined apparatus, the one piece of information may be information indicating a remedial measure for a fault condition that has occurred in a predetermined apparatus owned by a user, and each of the one or more nodes may correspond to a question as to whether or not the predetermined apparatus owned by the user exhibits a plurality of fault conditions.

As described above, in the search support method according to this embodiment, a network is presented to a user, the network including a plurality of questions and information that are connected to each other, the information being identified if affirmative answers to the questions are provided, and the display mode of the network is changed in accordance with the progress of the search. By seeing the presented network, the user can look through the questions and information to answer the questions displayed in the network. Thus, the user can search for one piece of information by providing affirmative answers to the questions independently of the order of sequential questions that are asked by using a decision tree. In this manner, the search support apparatus can suppress the user's feeling of anxiety or irksomeness at the time of engaging in questions and answers in search of desired information. Unless the user feels anxious or irksome, it is unnecessary to search for information again as a result of the anxiety or irksomeness, thereby avoiding an increase in the processing load and power consumption of the apparatus.

Second Embodiment

This embodiment further describes a technique for display based on the property of search target information in a search support apparatus, a search support method, and the like that can suppress a user's feeling of anxiety or irksomeness at the time of engaging in questions and answers in search of desired information.

Figures 19, 20:
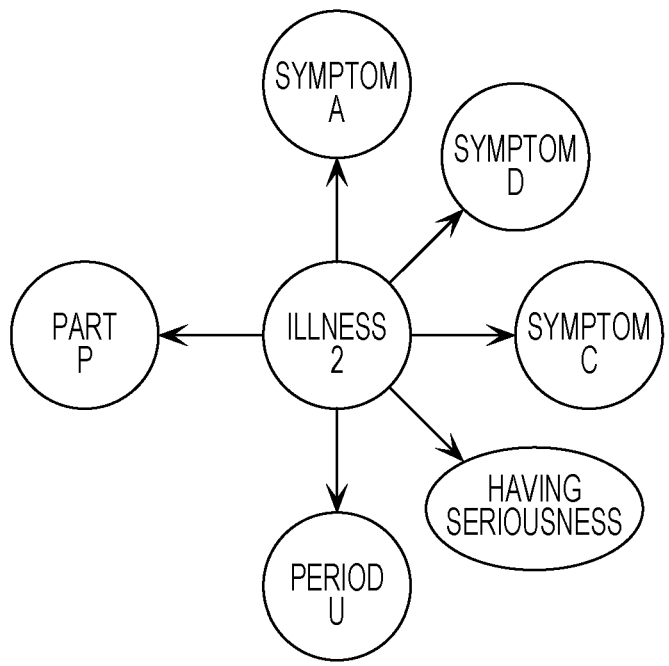
FIG. 19 is a second explanation diagram used to describe a method for identifying an illness on the basis of checking of accessory symptoms.
FIG. 20 illustrates a data table of illnesses in a second embodiment.

FIG. 19 is a second explanation diagram used to describe a method for identifying an illness on the basis of checking of obvious symptoms. As illustrated in FIG. 19, an illness 2 is associated with symptoms A, C, and D of the illness 2, a part P at which the illness 2 occurs, a period U over which a person has the illness 2, and the seriousness (degree of seriousness) of the illness 2. The association between the illness 2 and each item is different from the association between the illness 1 and each item in the first embodiment especially in that the seriousness of the illness 2 is associated.

The seriousness is an index indicating how serious an illness is. In this embodiment, illnesses are classified into serious illnesses and not serious illnesses, and then the illnesses classified as serious illnesses are associated with information indicating "having seriousness". It should be noted that the seriousness is an exemplary degree of importance indicating how important an illness is for a user.

A configuration of the search support apparatus in this embodiment is the same as or similar to the configuration of the search support apparatus 10 in the first embodiment.

FIG. 20 illustrates an illness data table D2 in this embodiment. The illness data table D2 is a table in which a plurality of illnesses and symptoms of the plurality of illnesses are associated with each other. The illness data table D2 indicates, in addition to the items indicated in the illness data table D1 in the first embodiment, "having seriousness" or "not having seriousness" as the seriousness of each of the illnesses. Specifically, illnesses 1, 3, and 4 do not have seriousness, and an illness 2 has seriousness.

Even if the symptoms that a person having a serious illness exhibits or does not exhibits are not the same as the symptoms that the user is exhibiting or is not exhibiting, in the case where the number of the symptoms that do not match is less than or equal to a predetermined number (e.g., one), the search support apparatus 10 according to this embodiment prevents the symptoms from being deleted from the network.

Next, a search method executed by the search support apparatus according to this embodiment will be described.

Figure 21A:
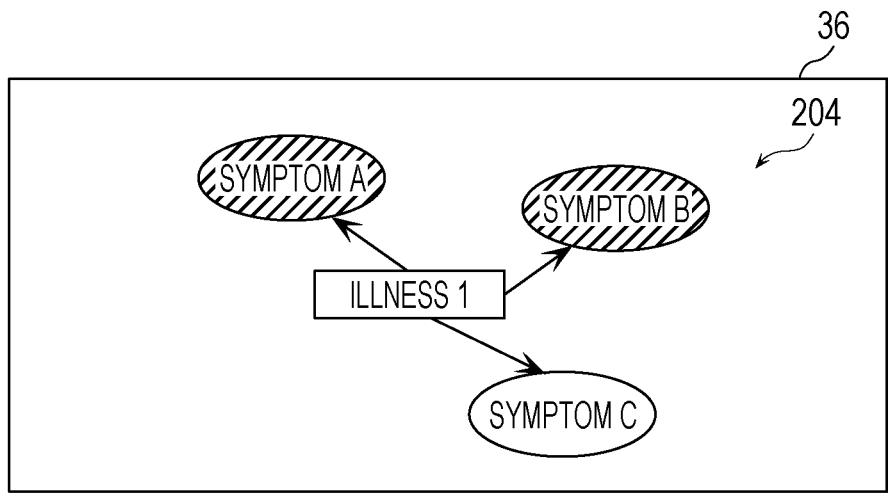
FIG. 21A illustrates a comparative example of a network displayed on a display device in the second embodiment.

FIG. 21A illustrates a comparative example of a network displayed on the display device 36 in this embodiment. Specifically, a network 204 illustrated in FIG. 21A is a network that is displayed on the display device 36 after a user has answered that symptoms A and B are exhibited to the search support apparatus 10.

In the network 204, a node corresponding to the illness 1 is displayed from among the illnesses 1 to 4, the illness 1 causing the symptoms A and B, and also nodes corresponding to symptoms A, B, and C caused by the illness 1 are displayed. In other words, the illness 2 is not displayed in the network 204 because the illness 2 does not cause the symptoms A and B. A symptom D caused by the illness 2 is not displayed in the network 204 either. Such display is performed because a node corresponding to the illness 2 has been deleted as a result of the fact that symptoms that a person having the illness 2 exhibits or does not exhibit are not the same as the symptoms that the user is exhibiting or is not exhibiting.

Figure 21B:
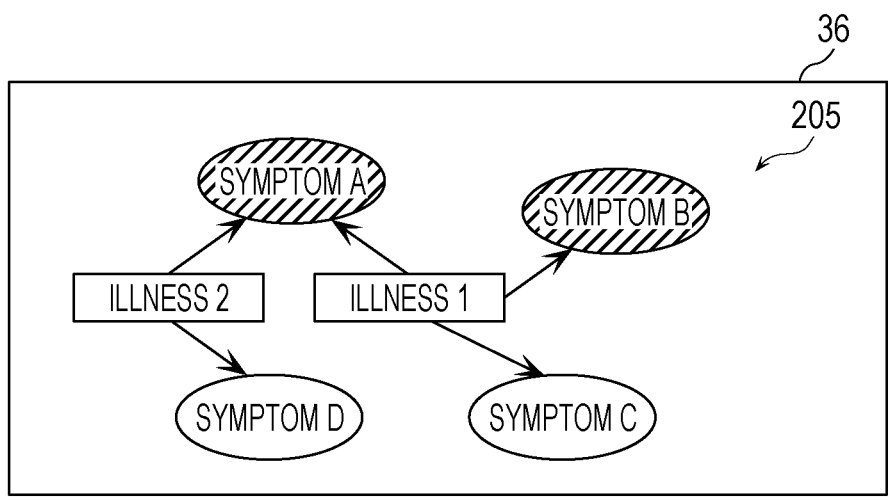
FIG. 21B illustrates an example of a network displayed on a display device in the second embodiment.

FIG. 21B illustrates an example of a network displayed on the display device 36 in this embodiment. As in the network 204, a network 205 illustrated in FIG. 21B is a network displayed on the display device 36 after the user has answered that the symptoms A and B are exhibited to the search support apparatus 10.

In the network 205, in addition to the nodes displayed in the network 204, a node corresponding to the illness 2 and a node corresponding to the symptom D caused by the illness 2 are displayed. This is because the number of symptoms that do not match is one although the symptoms that a person having the illness 2 exhibits or does not exhibits are not the same as the symptoms that the user is exhibiting or is not exhibiting, since the illness 2 is associated with information indicating "having seriousness". Then, the search support apparatus 10 continues asking questions to the user in accordance with the decision tree.

In the above manner, even if the information search has ended, if the degree of importance satisfies a certain condition and there is a remaining question for which an answer has not been acquired from a user, the search support apparatus further causes the display device 36 to display a network including a node corresponding to the remaining question. Accordingly, if the searched information is of great importance, for example, the search support apparatus can display the network corresponding to the remaining question to acquire a user's answer. The user can also see the network related to the remaining question. In the above manner, it is possible to suppress the user's feeling of anxiety or irksomeness.

Third Embodiment

This embodiment describes another configuration of the search support apparatus that can suppress a user's feeling of anxiety or irksomeness at the time of engaging in questions and answers in search of desired information.

Figure 22:
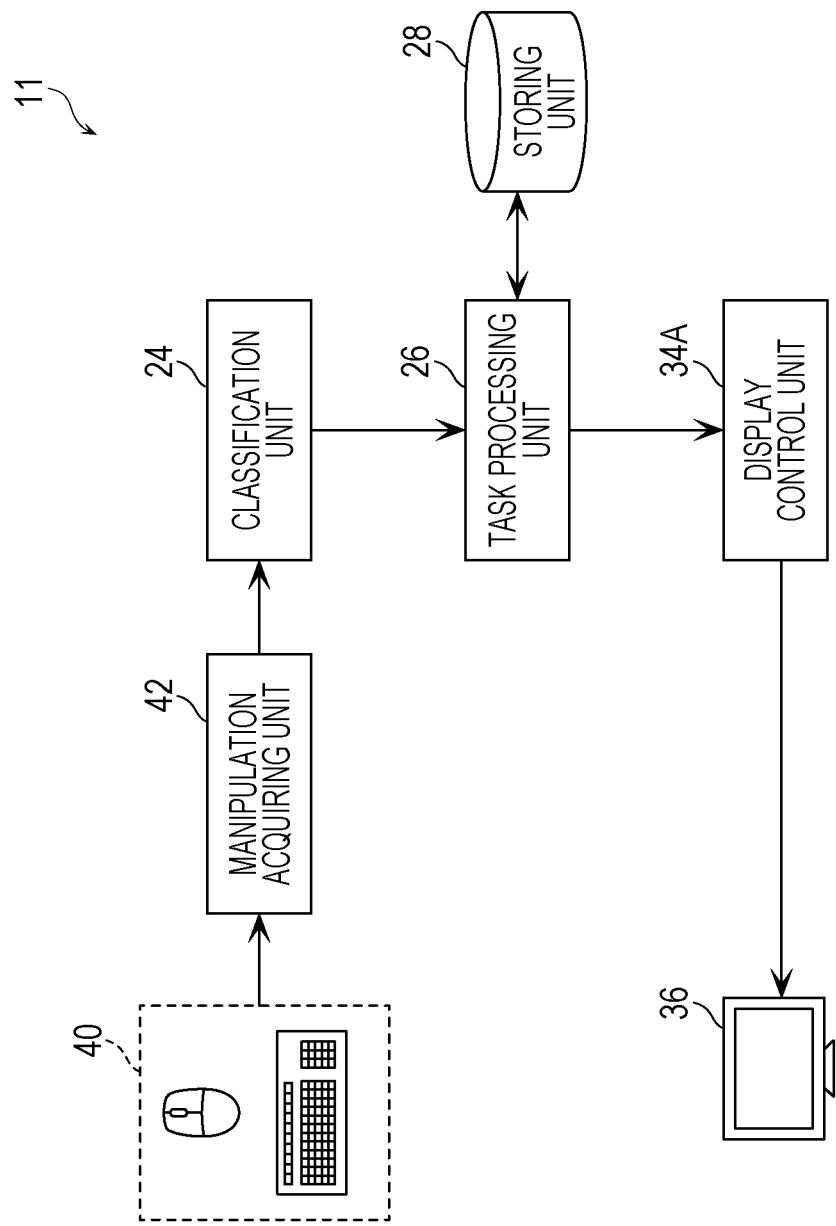
FIG. 22 is a block diagram illustrating a configuration of a search support apparatus according to a third embodiment.

FIG. 22 is a block diagram illustrating a configuration of a search support apparatus 11 according to this embodiment.

As illustrated in FIG. 22, the search support apparatus 11 according to this embodiment does not include the microphone 20, the speech recognition unit 22, the speech synthesis unit 30, and the speaker 32, which are included in the search support apparatus 10 in the first embodiment. Instead, the search support apparatus 11 includes a manipulation interface 40 and a manipulation acquiring unit 42. In addition, the search support apparatus 11 includes a display control unit 34A instead of the display control unit 34. It should be noted that the search support apparatus 11 may be configured in such a manner that the above components are contained in a single housing or that the above components are arranged to be dispersed and connected to each other via a network or the like so that communication can be performed, as in the first embodiment.

The manipulation interface 40 is a user interface for receiving manipulations made by the user on the search support apparatus 11. Specifically, the manipulation interface 40 is a mouse, a keyboard, a touch panel, or the like and receives clicking of a button, pressing of a key, movement of the mouse or a user's finger on the touch panel, or the like.

The manipulation acquiring unit 42 acquires the user's manipulations (e.g., the position selected on a screen and an input character string) received by the manipulation interface 40, and generates, on the basis of the acquired manipulations, text data as the user intends, to provide the text data to the classification unit 24.

The display control unit 34A has the function of the display control unit 34 and, in addition, causes the display device 36 to display a question to the user.

Accordingly, the search support apparatus 11 can cause the display device 36 to display a question to be presented to the user instead of having interactions by using speech and can receive an answer from the user to the question by using the manipulation interface 40, thereby having interactions with the user. Accordingly, the search support apparatus 11 can suppress the respondent's feeling of anxiety or irksomeness at the time of engaging in questions and answers in search of desired information.

It should be noted that in each of the above-described embodiments, each component may be implemented by configuring dedicated hardware or by executing a software program suitable for the component. Each component may also be implemented by a program executing unit, such as a central processing unit (CPU) or a processor reading out and executing a software program stored in a recording medium, such as a hard disk or semiconductor memory.

Although the embodiments of the search support apparatus and the like according to one or more aspects have been described above, the present disclosure is not limited to the above embodiments. An embodiment that is modified in various manners that a person skilled in the art will arrive at or an embodiment configured by a combination of components in different embodiments may also be included in the range of the one or more aspects without departing from the spirit of the present disclosure.

The present disclosure is applicable to a search support apparatus that can suppress a user's feeling of anxiety or irksomeness at the time of engaging in questions and answers in search of desired information. More specifically, the present disclosure is applicable to a search support apparatus that can suppress a user's feeling of anxiety or irksomeness in search of an illness, a real estate property, an itinerary, a remedial measure for a fault condition, or the like.

What is claimed is:

1. A control method executed by a processor for controlling a display connected to the processor and a memory, the processor being connected to an input that receives an inputted answer to a presented question, the control method comprising:

causing the display to display a network diagram, the network diagram being stored in the memory and including a plurality of nodes of a first type corresponding to a plurality of symptoms and a plurality of nodes of a second type corresponding to a plurality of illnesses, the plurality of nodes of the second type each being linked to one or more related nodes of the first type among the plurality of nodes of the first type via a connection line;

causing the display to emphasize a display of a first node of the first type corresponding to the presented question, the presented question asking about presence or absence of one symptom among the plurality of symptoms, the first node corresponding to the one symptom;

acquiring the inputted answer to the presented question from the input, the inputted answer being input to the input by a user;

determining an answer to the presented question from the inputted answer;

if it is determined that the user has answered that the one symptom is present, causing the display to delete all nodes from the network diagram except for the first node, one or more second nodes of the second type directly linked to the first node, and one or more third nodes of the first type directly linked to the one or more second nodes of the second type directly linked to the first node; and causing the display to display the network diagram during sequential questions, the sequential questions being asked in search of one piece of information.

2. The control method according to claim 1, further comprising:

determining whether or not a number of the one or more second nodes of the second type directly linked to the first node is less than or equal to a predetermined number; and if it is determined that the number of the one or more second nodes of the second type directly linked to the first node is greater than the predetermined number, repeating a process until the number of the one or more second nodes of the second type directly linked to the first node becomes less than or equal to the predetermined number, the process including causing the display to emphasize display, acquiring the inputted answer, determining the answer, causing the display to perform deletion, and determining whether or not the number of the one or more second nodes of the second type directly linked to the first node is less than or equal to the predetermined number.

3. The control method according to claim 2, wherein the predetermined number is one.

4. The control method according to claim 3, wherein the memory further stores first information and second information, the first information indicating each of the plurality of illnesses and a degree of seriousness of a corresponding illness, the second information indicating a question to be presented to the user, the control method further comprising:

if it is determined that the one or more second nodes of the second type directly linked to the first node include a single second node, determining whether or not a degree of seriousness of an illness corresponding the single second node is greater than or equal to a threshold based on the first information; and if it is determined that the degree of seriousness of the illness corresponding to the single second node is greater than or equal to the threshold, causing the display to display at least a first node that does not correspond to the presented question based on the second information.

5. The control method according to claim 1, further comprising:

determining whether or not a number of the one or more second nodes of the second type directly linked to the first node is less than or equal to a predetermined number; and if it is determined that the number of the one or more second nodes of the second type directly linked to the first node is greater than the predetermined number, prohibiting the display from displaying the network diagram.

6. The control method according to claim 1, wherein the display is a first display device for a doctor who is in charge of a diagnosis of an illness of the user, and the processor is connected to a second display device for the user, the second display device being different from the first display device, the control method further comprising:

causing the second display device to perform a same display as the first display device.

7. The control method according to claim 1, wherein the display is a first display device for a doctor who is in charge of a diagnosis of an illness of the user, and the processor is connected to a second display device for the user, the second display device being different from the first display device, the control method further comprising:

preventing the second display device from performing a same display as the first display device.

8. The control method according to claim 1, wherein the input includes at least one of a microphone, a keyboard, and a touch panel.

9. The control method according to claim 1, wherein, in the display of the decision tree:

the first node is configured to be displayed in a first manner if the user has answered that the one symptom is present;

the first node is configured to be displayed in a second manner if the user has answered that the one symptom is absent;

the first node is configured to be displayed in a third manner if the presented question is asked and the inputted answer is not acquired from the input;

each of the plurality of nodes of the first type other than the first node and each of the plurality of nodes of the second type for which inputted answers to presented questions are not acquired are displayed in a fourth manner before the presented questions are asked; and the first manner, the second manner, the third manner, and the fourth manner are different.

10. A non-transitory computer-readable recording medium storing a program for causing a processor to execute the control method according to claim 1.

11. A control device that is connected to a display and an input, the input receiving an inputted answer to a presented question, the control device comprising:

a processor; and a memory, wherein the processor causes the display to display a network diagram, the network diagram being stored in the memory and including a plurality of nodes of a first type corresponding to a plurality of symptoms and a plurality of nodes of a second type corresponding to a plurality of illnesses, the plurality of nodes of the second type each being linked to one or more related nodes of the first type among the plurality of nodes of the first type via a connection line, causes the display to emphasize a display of a first node of the first type corresponding to the presented question that asks about presence or absence of one symptom among the plurality of symptoms, the first node corresponding to the one symptom, acquires the inputted answer to the presented question from the input, the inputted answer being input to the input by a user, determines an answer to the presented question from the inputted answer, if it is determined that the user has answered that the one symptom is present, causes the display to delete all nodes from the network diagram except for the first node, one or more second nodes of the second type directly linked to the first node, and one or more third nodes of the first type directly linked to the one or more second nodes of the second type directly linked to the first node, and causes the display to display the network diagram during sequential questions, the sequential questions being asked in search of one piece of information.

* * * * *